United States Patent [19]

Stahelin

[11] Patent Number: 5,695,497

[45] Date of Patent: Dec. 9, 1997

[54] SCREW MADE OF BIODEGRADABLE MATERIAL FOR BONE SURGERY PURPOSES, AND SCREWDRIVER SUITABLE THEREFOR

[76] Inventor: Andreas C. Stahelin, St. Alban-Vorstadt 51, CH-4059 Basel, Switzerland

[21] Appl. No.: 412,307

[22] Filed: Mar. 29, 1995

Related U.S. Application Data

[63] Continuation-in-part of Ser. No. 309,311, Sep. 20, 1994.

[30] Foreign Application Priority Data

Mar. 29, 1994 [CH] Switzerland ............... 00938/94
Dec. 12, 1994 [CH] Switzerland ............... 03757/94

[51] Int. Cl.⁶ ............................................. A61B 17/58
[52] U.S. Cl. ................................. 606/73; 606/104
[58] Field of Search ........................... 606/73, 77, 104, 606/65, 66, 76; 411/393, 395, 403, 410; 81/436

[56] References Cited

U.S. PATENT DOCUMENTS

| | | | |
|---|---|---|---|
| 5,139,499 | 8/1992 | Small et al. | 606/104 |
| 5,169,400 | 12/1992 | Mühling et al. | 606/77 |
| 5,269,209 | 12/1993 | Baker . | |
| 5,364,400 | 11/1994 | Rego, Jr. et al. | 606/77 |

FOREIGN PATENT DOCUMENTS

| | | |
|---|---|---|
| 0502698 | 9/1992 | European Pat. Off. . |
| 8804456 | 6/1988 | Germany . |
| 2022482 | 12/1979 | United Kingdom . |

*Primary Examiner*—Michael Buiz
*Assistant Examiner*—Julian W. Woo
*Attorney, Agent, or Firm*—Cushman Darby & Cushman Intellectual Property Group of Pillsbury Madison & Sutro LLP

[57] ABSTRACT

In a screw made of biodegradable material for bone surgery purposes, the outer surface of the screw body is provided with a coaxial external thread. A coaxial channel of sawtoothed star-shaped transverse cross-sectional profile is provided in the screw body, which channel is open at the proximal end in order to receive the complementarily shaped shaft of a screwdriver, and extends into the area of the distal end. The channel wall is radially symmetrical about the longitudinal axis in regular rotary steps and defines an axial channel area and a plurality of lobe areas arranged uniformly around the channel area. In each lobe area the channel wall has a pair of flanks which extend into the vicinity of an end of the lobe area remote from the channel area. In a cross-section of the screw body, each lobe area is formed asymmetrical in respect of a diametrical plane. A section of the contour line which corresponds to the leading flank is shorter than a section of the contour line which corresponds to the trailing flank. The leading flank may have a form which leads to an increasing extent as the radial distance increases in the direction of screwing-in. At the end of the lobe area the flanks can run together to form an edge and define 3 to 8, preferably 6, sickle-shaped teeth which are salient with respect to the direction of rotation.

20 Claims, 23 Drawing Sheets

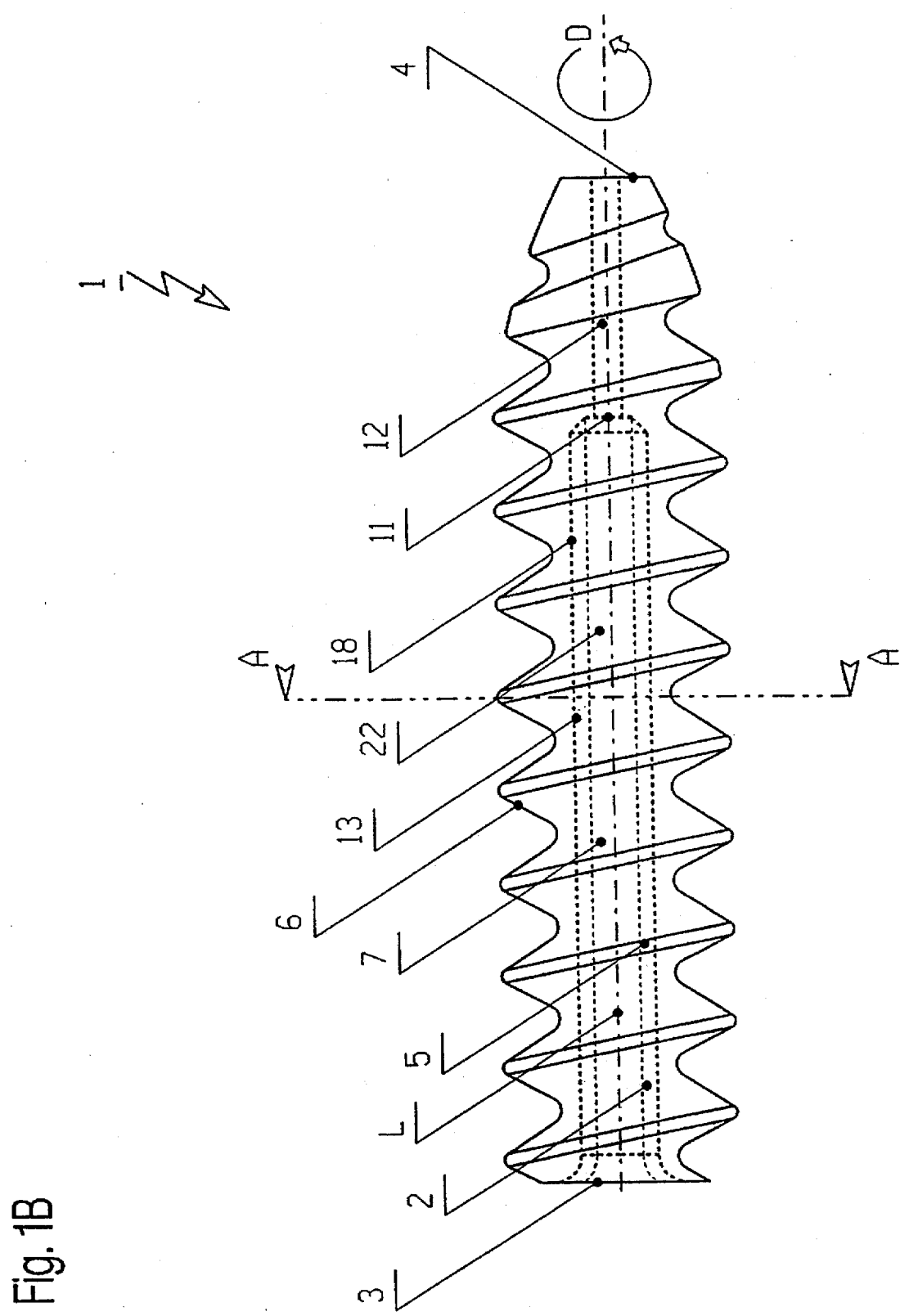

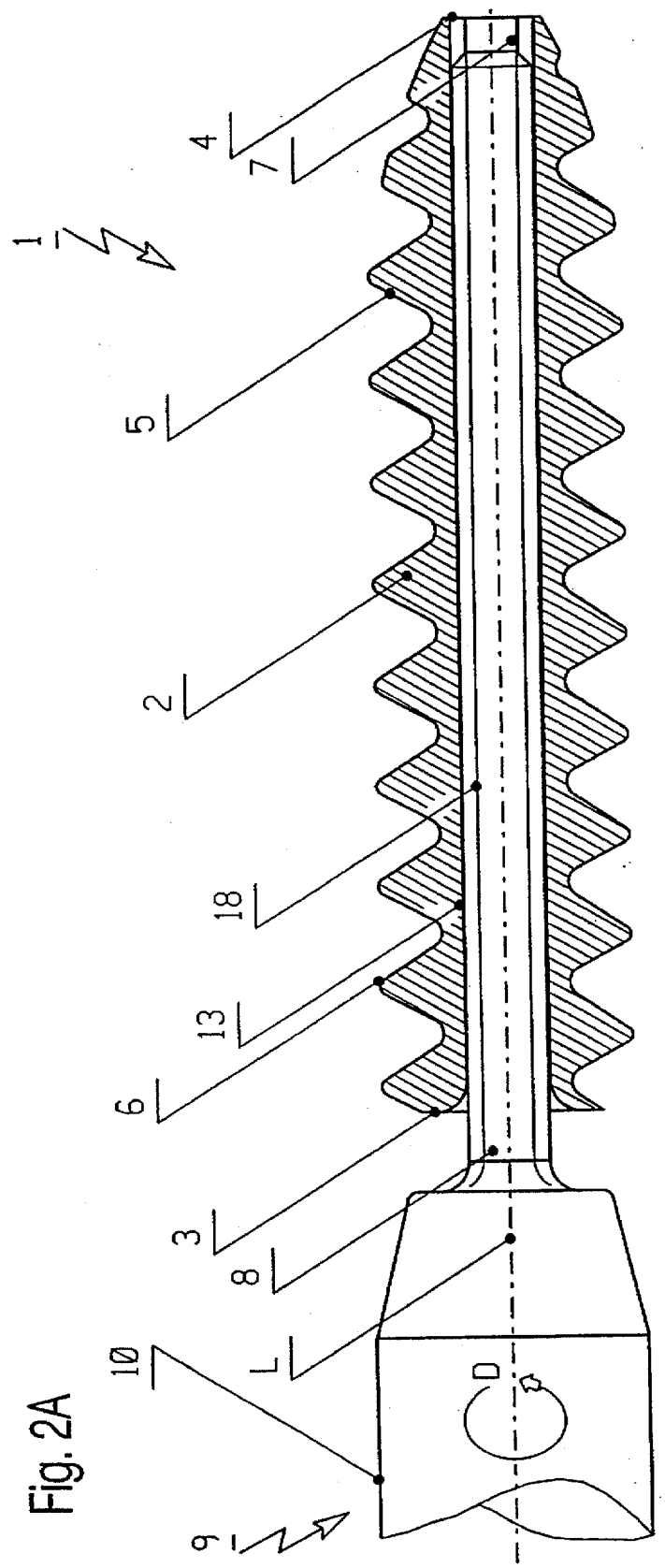

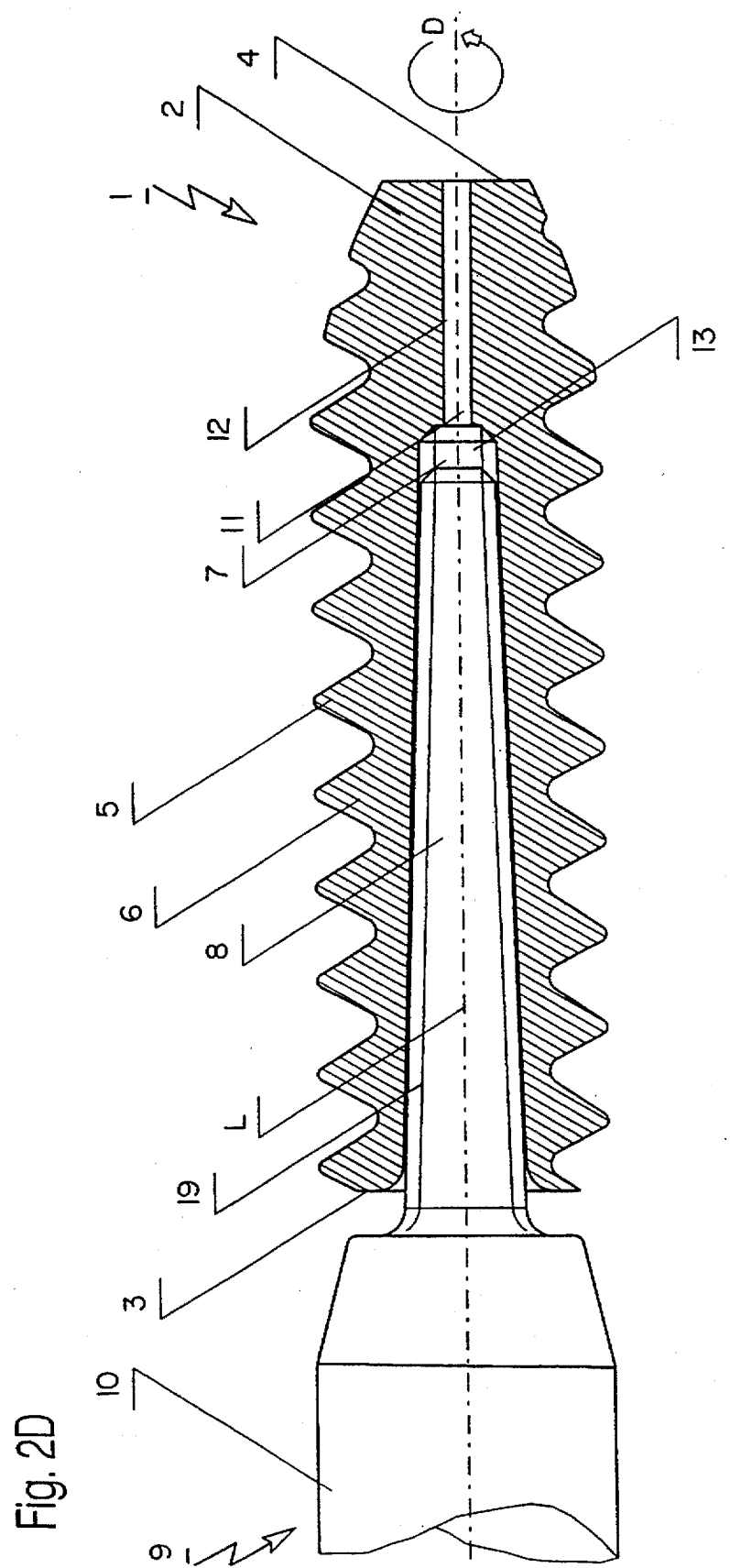

SCREW MADE OF BIODEGRADABLE MATERIAL FOR BONE SURGERY PURPOSES, AND SCREWDRIVER SUITABLE THEREFOR

REFERENCE TO RELATED APPLICATION

This is a continuation-in-part of application Ser. No. 08/309,311, filed Sep. 20, 1994.

BACKGROUND OF THE INVENTION

The invention relates to a screw made of biodegradable material for bone surgery purposes, having an elongate screw body which extends, in the direction of a longitudinal axis thereof, between a proximal and a distal end thereof, and in which:

- an outer surface of the screw body is provided with an external thread coaxial with respect to the longitudinal axis, which external thread is intended for guiding and holding the screw on bone material of a patient and defines a direction of rotation about the longitudinal axis for the screwing-in of the screw body and advancing of the distal end into the bone material,
- an elongate channel coaxial with respect to the longitudinal axis is provided in the screw body, which channel is open at the proximal end for receiving a shaft of a screwdriver intended for turning the screw,
- the channel has a channel wall, the shape of which is rotationally symmetrical about the longitudinal axis in discrete, regular rotary steps and provides, in a cross-section of the screw body at right angles to the longitudinal axis, a trace line which is a closed contour line radially symmetrical about a trace line of the longitudinal axis in discrete, regular rotary steps,
- the channel wall defines an axial channel area and a plurality of lobe areas arranged uniformly about the channel area, so that the channel consists essentially of the combination of the axial channel area and the lobe areas, and
- in each lobe area the channel wall has a pair of flanks which extend essentially from the channel area to the vicinity of an end of the lobe area remote from the channel area, and which, with reference to the direction of rotation, define in each case a leading flank and a trailing flank.

The invention also relates to a screwdriver for driving this screw into bone material of a patient during bone surgery, the screwdriver being provided with a grip and with an elongate shaft secured thereon, and it being possible for the shaft to be introduced into the channel of the screw and removed therefrom.

A screw made of biodegradable material, for bone surgery purposes, is known from, for example, EP-A-0,502,698.

The material of the screw which is, as has been mentioned in the introduction, biodegradable, i.e. capable of being absorbed in the body of a patient, is known from EP-A-0, 502,698 as well as from DE-A-2,742,128 and EP-A-0,011, 528. This screw material is essentially a polylactide, a polyglycolide or a copolymer thereof, which is exceptionally formable, sterilizable and absorbable.

However, this screw material is also brittle, which leads to problems when using the screw. When driving the screw into the bone material of a patient during bone surgery, the screwdriver transmits, to the screw, forces which can load the brittle screw material to an excessive extent, with the result that the screw is damaged. In the case of hard bone, for example, there is a risk of the screwdriver slipping in the screw.

To solve the problems which have been mentioned, a large number of star-shaped configurations of the channel and of its trace line in the cross-section of the screw body have been proposed. However, this very multiplicity of forms points to the fact that no previous screw has as yet proven satisfactory. In the known forms of the channel, the adjoining, force-transmitting flanks of the lobe areas of the screw and of the screwdriver are oriented in such a way that when the screw is driven into bone material, radially outwardly directed components of the force occur on these flanks. Expansive forces therefore act on the body of the screw, which forces tend to snap the screw.

SUMMARY OF THE INVENTION

Accordingly, the object of the invention is to provide a screw of the type mentioned in the introduction and a screwdriver suitable therefor, with which the cited disadvantages of the known screws and of the screwdrivers suitable therefor are overcome.

To achieve this object, the invention is based on the understanding that forces are to be exerted on the screw only in the direction of driving-in. In bone surgery, a screw of the type mentioned in the introduction which has a good fit scarcely ever needs to be removed. If such a screw does have to be removed, then it is generally because it does not have a good fit, in which case it by definition has a loose fit and, as a result, no appreciable forces have to be exerted thereon, in the direction counter to driving-in, in order to unscrew it. Therefore, there is absolutely no need for the screw to be symmetrical in respect of a diametrical plane passing through its longitudinal axis as was the case up to now in the prior art.

On the basis of this understanding, the stated object is achieved according to the invention, in the case of a screw of the type mentioned in the introduction, by virtue of the fact that the channel extends into the area of the distal end, and, in a cross-section of the screw body at right angles to the longitudinal axis, each lobe area is formed asymmetrical in respect of a diametrical plane passing through the longitudinal axis, a section of the contour line which corresponds to the leading flank being shorter than a section of the contour line which corresponds to the trailing flank, so that the lobe area has a sawtooth-like profile of a radial distance of the contour line from the longitudinal axis when considered along the contour line with, on the average, a steeper raise of the leading flank and a flatter fall of the trailing flank.

A screwdriver according to the invention and of the type mentioned in the introduction is characterized in that the shaft has a form matching the channel in a complementary manner.

In the case of the screw according to the invention, the transmission of the force from the screwdriver according to the invention to the screw is optimal to the extent that the screwdriver does not slip in the screw, even in the event of large torques. The body of the screw made of brittle material is acted upon by smaller expansive forces than up to now in the prior art with radially symmetrical screws, which is optimally adapted to the material of the screw. Thus, when it is screwed into bone material, a screw according to the invention tolerates greater torques than was admissible with the previous screws. The body of the screw does not need to be solid in order to tolerate the torques, and for this reason the channel can extend right into the vicinity of and, if appropriate, right up to the distal end, which in turn allows the torques to be transmitted to the screw and distributed uniformly, essentially over the entire length thereof.

Thus, it is possible in many cases, even with hard bone, to dispense with the preliminary cutting of a thread in the bone, which considerably simplifies the working procedure of a bone operation.

The preferred embodiments specified hereinbelow guarantee, in various alternatives, an optimal orientation or deflection of the forces exerted by the screwdriver on the screw, so that no expansive forces act on the screw body, but instead only tension and shear.

In a preferred embodiment of the screw according to the invention, in each lobe area, at least one of the flanks exhibits, at least in the vicinity of the end of the lobe area, a form which leads to an increasing extent in the direction of rotation as the radial distance from the longitudinal axis increases.

In this embodiment of the screw according to the invention, no expansive forces act on the screw body made of brittle material, but instead only tension and shear.

In a preferred embodiment, the two flanks in each lobe area are at a distance from one another which tapers towards the end of the lobe area as the radial distance from the longitudinal axis increases. The two flanks can preferably run together at the end of the lobe area to form an edge.

In another preferred embodiment, the leading flank in each lobe area is curved convexly with respect to the direction of rotation, or the leading flank is essentially located in a plane passing through the longitudinal axis.

In yet another preferred embodiment, the leading flank in each lobe area is curved concavely with respect to the said direction of rotation, at least in the vicinity of the end of the lobe area.

In yet another preferred embodiment, the trailing flank is curved convexly counter to the direction of rotation, at least in the vicinity of the end of the lobe area.

In a preferred combination of the embodiments mentioned above, it is possible, in a cross-section of the screw body at right angles to the longitudinal axis, for the contour line to correspond essentially to a star-shaped continuous line radially symmetrical about the trace line of the longitudinal axis, with 3 to 8, and preferably 6, optionally sickle-shaped teeth salient with respect to the direction of rotation.

In another, again preferred, combination of the embodiments mentioned above it is possible, in a cross-section of the screw body at right angles to the longitudinal axis, for the contour line to correspond essentially to a bucketwheel-shaped continuous line rotationally symmetrical about the trace line of the longitudinal axis, with 3 to 8, and preferably 6, optionally approximately sickle-shaped lobes salient with respect to the direction of rotation.

In another preferred embodiment, the two flanks in each lobe area are at an approximately constant distance from one another. In this case, in a cross-section of the screw body at right angles to the longitudinal axis, the contour line can preferably correspond essentially to a bucketwheel-shaped continuous line rotationally symmetrical about the trace line of the longitudinal axis, with 3 to 8, and preferably 6, lobes which are salient with respect to the direction of rotation, are approximately in the form of a ring segment, and are of approximately constant width.

In yet another preferred embodiment, a trace line of the leading flank is inclined essentially in a straight line and with respect to the direction of rotation in each lobe area, in a cross-section of the screw body at right angles to the longitudinal axis. The inclination of the leading flank can in this case preferably be up to 10° and preferably about 5°.

In a first preferred development of one of the embodiments mentioned above, the flanks are twisted helically about the longitudinal axis with respect to the direction of rotation, in such a way that, in two cross-sections of the screw body which are different from one another and at right angles to the longitudinal axis, the contour lines represent congruent images of one another which can be made congruent by simple turning about the trace line of the longitudinal axis. In this way, a twisted contact surface is formed between the screw body and the shaft of the screwdriver, which contact surface deflects the rotational forces exerted by the screwdriver on the screw in such a way that, when it is screwed in, the screw according to the invention tolerates even greater torques than in the case of a straight axial design of the contact surface.

In a second preferred development of one of the embodiments mentioned above, the flanks are tapered in the direction from the proximal to the distal end in such a way that, in two cross-sections of the screw body which are different from one another and at right angles to the longitudinal axis, the contour lines represent of one another which can be made congruent by homothetic transformation about the trace line of the longitudinal axis. The shaft of the screwdriver can thereby be dimensioned in such a way that it fits without play into the channel of the screw and yet can be easily withdrawn from the screw body, which is of great benefit, particularly in the case of an embodiment having the twisted contact surface mentioned above. If it is also intended that the channel should not extend quite up to the distal end of the screw body, then the shaft of the screwdriver inserted into the screw fills the channel of the screw body exactly, not only in the cross-section at right angles to the longitudinal axis, but also in the direction of the longitudinal axis, until the free end of the screwdriver bears on the distal end-point of the channel, as a result of which it is possible to reliably prevent the shaft of the screwdriver from spreading the screw body like a dowel and thereby breaking the brittle screw material.

In a preferred combination of the first and second developments, the flanks are both twisted and tapered in such a way that, in two cross-sections of the screw body which are different from one another and at right angles to the longitudinal axis, the contour lines represent images of one another which can be made congruent by a combination of simple turning and homothetic transformation about the trace line of the longitudinal axis.

The tapering in the direction from the proximal to the distal end preferably corresponds to a semi-aperture angle of up to 10° and preferably of approximately 2°. In the case of such dimensioning of the tapering, a breaking of the screw body by the shaft of the screwdriver is also prevented even when the channel extends continuously up to the distal end of the screw body and is open there, or even if the distal end-point of the channel yields under the pressure of the shaft of the screwdriver.

BRIEF DESCRIPTION OF THE DRAWINGS

Exemplary embodiments of the invention are explained in greater detail hereinbelow with reference to the drawings, in which:

FIGS. 1A to 1H respectively show first through eighth embodiments of a screw according to the invention, in side view;

FIGS. 2A to 2H show the embodiments of the screw according to the invention, in accordance with the corresponding FIGS. 1A to 1H, in longitudinal section and with a screwdriver according to the invention inserted therein and shown in a broken view;

DETAILED DESCRIPTION

Figure 1A:
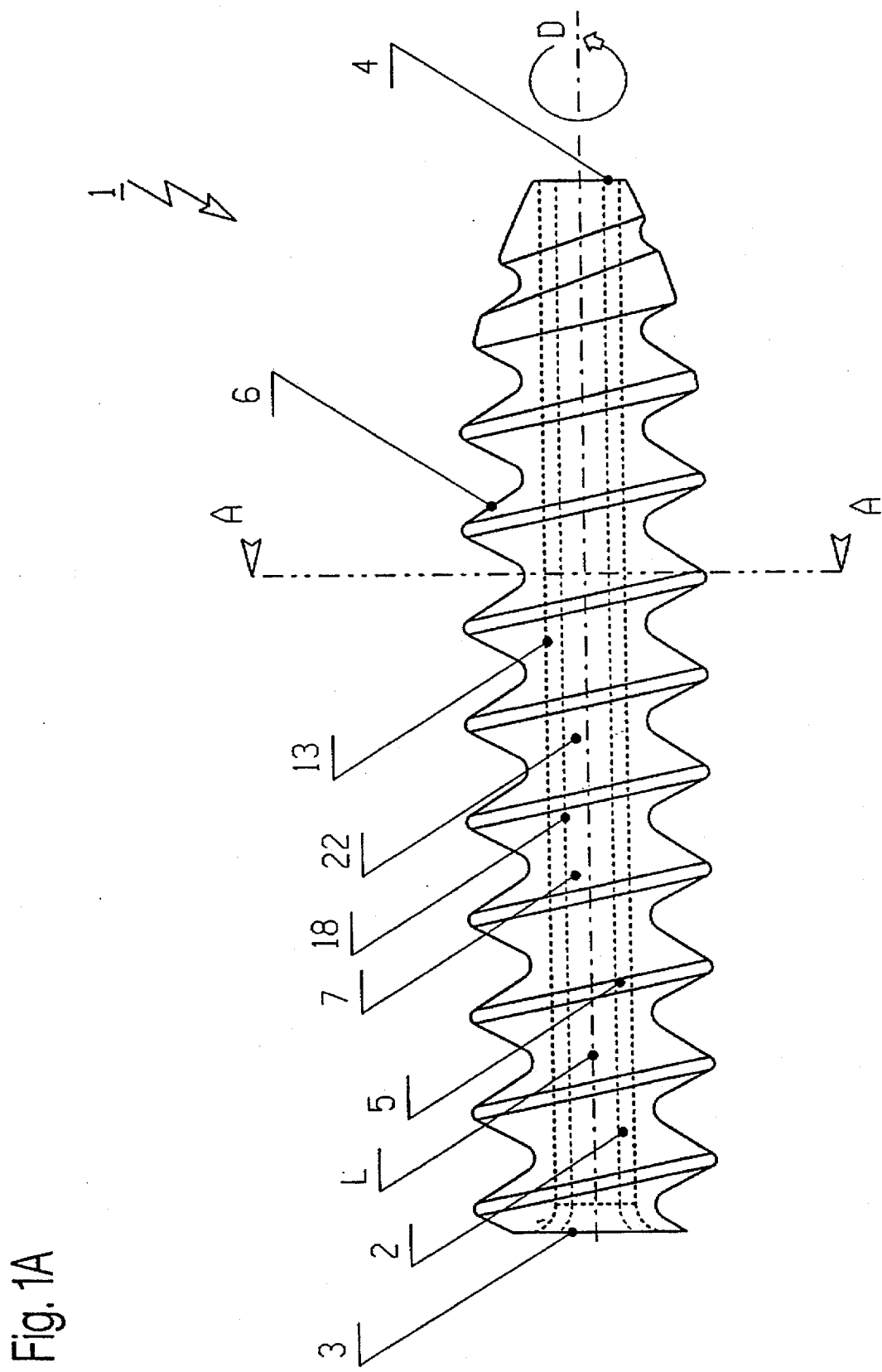

The screws according to the invention which are shown in the figures are made, for example, of a biodegradable material for bone surgery purposes. An example of such a material which may be mentioned here is the commercially available material marketed under the trademark PHU-SILINE by the company ArgoMedical AG, CH-6330 Cham, although this does not rule out the use of other biodegradable materials. This biodegradable material is worked to the desired shape in a known manner, for example by injection moulding, hot forming, hot press moulding and similar processes at a temperature suitable for this, which temperature is, in most cases, to be chosen in the range between room temperature and 100° C.

In FIGS. 1A to 1H, a screw 1 is shown in side view. A screw body 2 of the screw 1 extends in the direction of a longitudinal axis L of the screw 1 between a proximal end 3 and a distal end 4 of the screw 1 and of the screw body 2. An outer surface 5 of the screw body 2 is provided with an external thread 6 which is coaxial with respect to the longitudinal axis and is intended for guiding and holding the screw 1 on bone material of a patient. The pitch of the external thread 6 defines a direction of rotation D about the longitudinal axis L, in which direction the screw or the screw body 2 is screwed in, the distal end 4 of the screw body 2 advancing into the bone material.

A screw 1 of the type described above is shown in longitudinal section in each of FIGS. 2A to 2H.

A channel 7 which is coaxial with respect to the longitudinal axis L is provided in the screw body 2. This channel 7 extends into the area of the distal end 4: in the embodiments according to FIGS. 1A, 1C, 1E and 1G and also 2A, 2C, 2E and 2G right up to the distal end 4, and in the embodiments according to FIGS. 1B, 1D, 1F and 1H and also 2B, 2D, 2F and 2H only as far as the vicinity of the distal end 4. In the last-mentioned case, there extends, between an end 11 of the channel 7 and the distal end 4, a circular cylindrical auxiliary channel 12 which is coaxial with respect to the longitudinal axis L and whose role is explained further below.

At the proximal end 3, the channel 7 is open to the outside in order to be able to receive a shaft 8 of a screwdriver 9. In FIGS. 2A to 2H, the shaft 8 is shown, in side view, fitted coaxially in the channel 7 of the screw body 2, while the screwdriver 9 is provided with a coaxial grip 10 which is shown in a broken view. The shaft 8 has a form matching the channel 7 in a complementary manner, which form is explained in greater detail below. With the aid of the grip 10, the shaft 8 of the screwdriver 9 can be introduced into the channel 7 and removed therefrom, and the screwdriver 9 (with the shaft 8 introduced into the channel 7) can be operated in order to turn the screw 1.

The auxiliary channel 12 according to FIGS. 1B, 1D, 1F and 1H and also 2B, 2D, 2F and 2H prevents the shaft 8, when introduced into the channel 7, from acting as a piston and compressing air in the channel 7. Thus, when introducing the shaft 8 into the channel 7, no air in a gap between the shaft 8 and the channel 7 needs to escape, and this makes it possible to leave only a very small clearance between the shaft 8 and the channel 7 or a channel wall 13 of the channel 7, and consequently to guarantee an optimal transmission of the force from the screwdriver 9 to the screw 1. In addition, the auxiliary channel 12 can serve, in a manner known, for example from U.S. Pat. No. 4,950,270, as a passage for a guide pin or a guide wire, if the shaft 8 of the screwdriver 9 is correspondingly channelled.

In the embodiments according to FIGS. 1A and 2A and also 1B and 2B, the channel 7 and the shaft 8 have rectilinear generating lines (i.e., generatrice) 18, which are parallel with respect to the longitudinal axis L. The channel 7 and the shaft 8 can therefore be inscribed in a cylindrical enveloping volume.

Figure 1C:
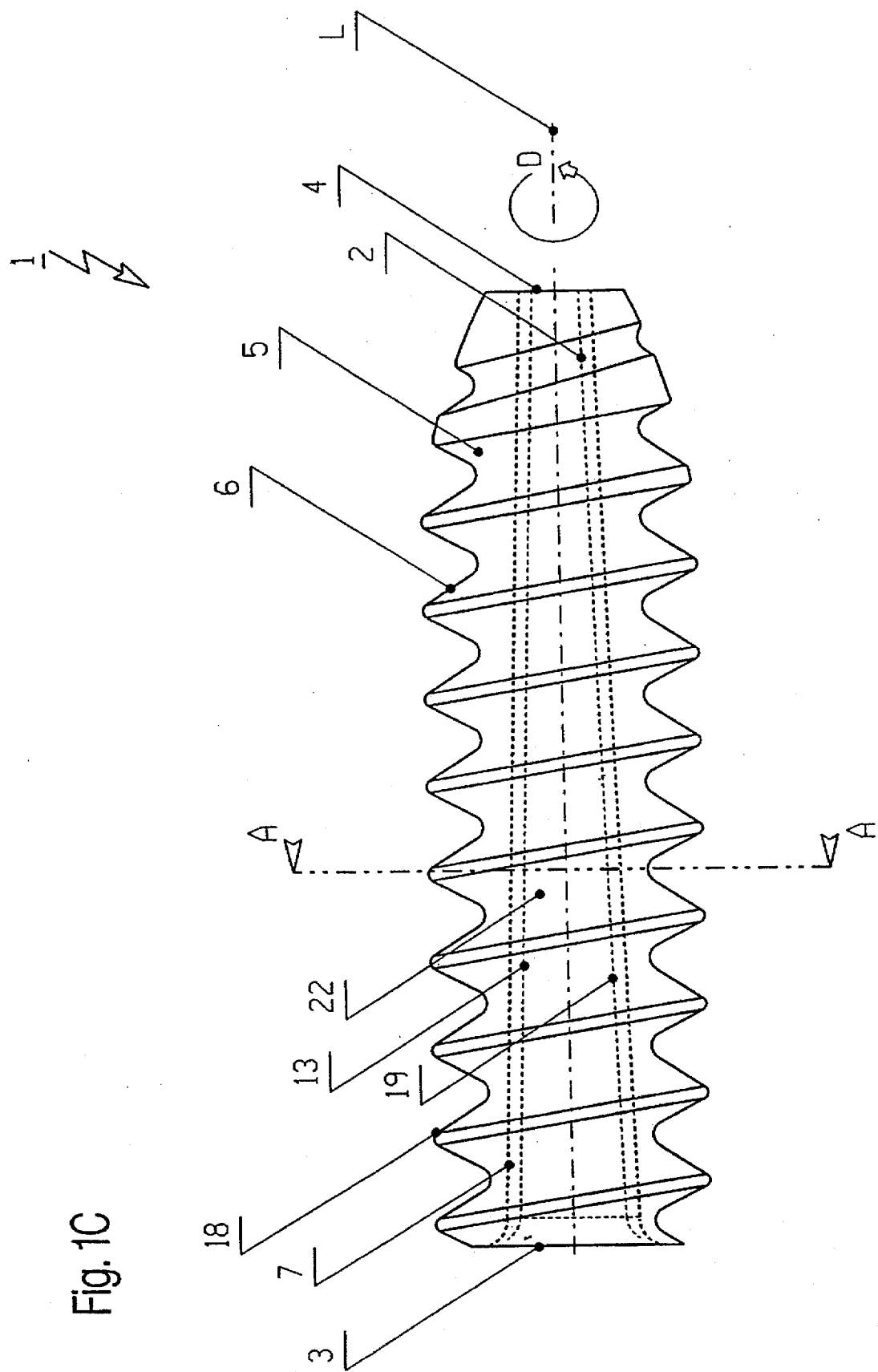
Figure 1D:
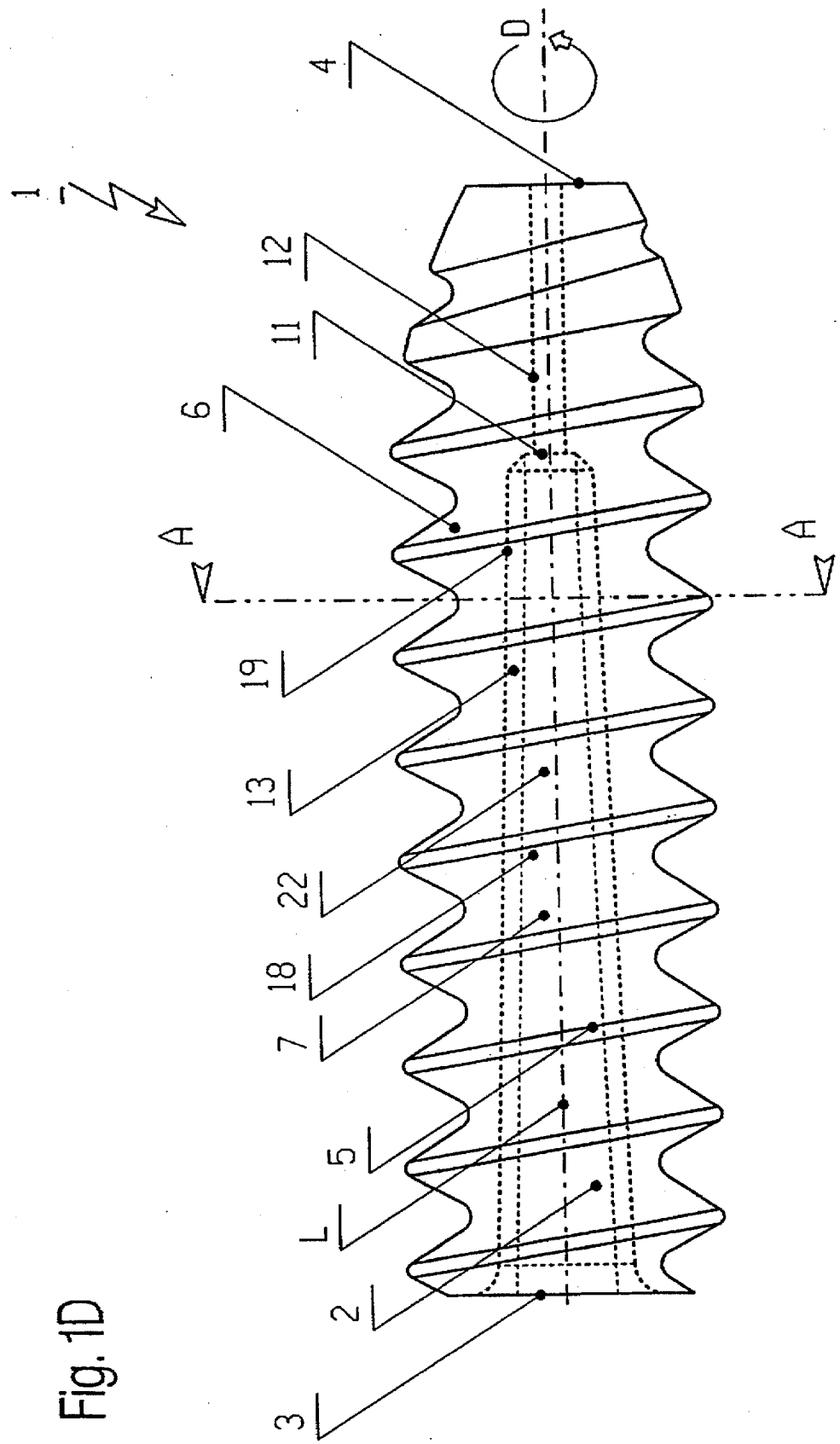
Figure 2B:
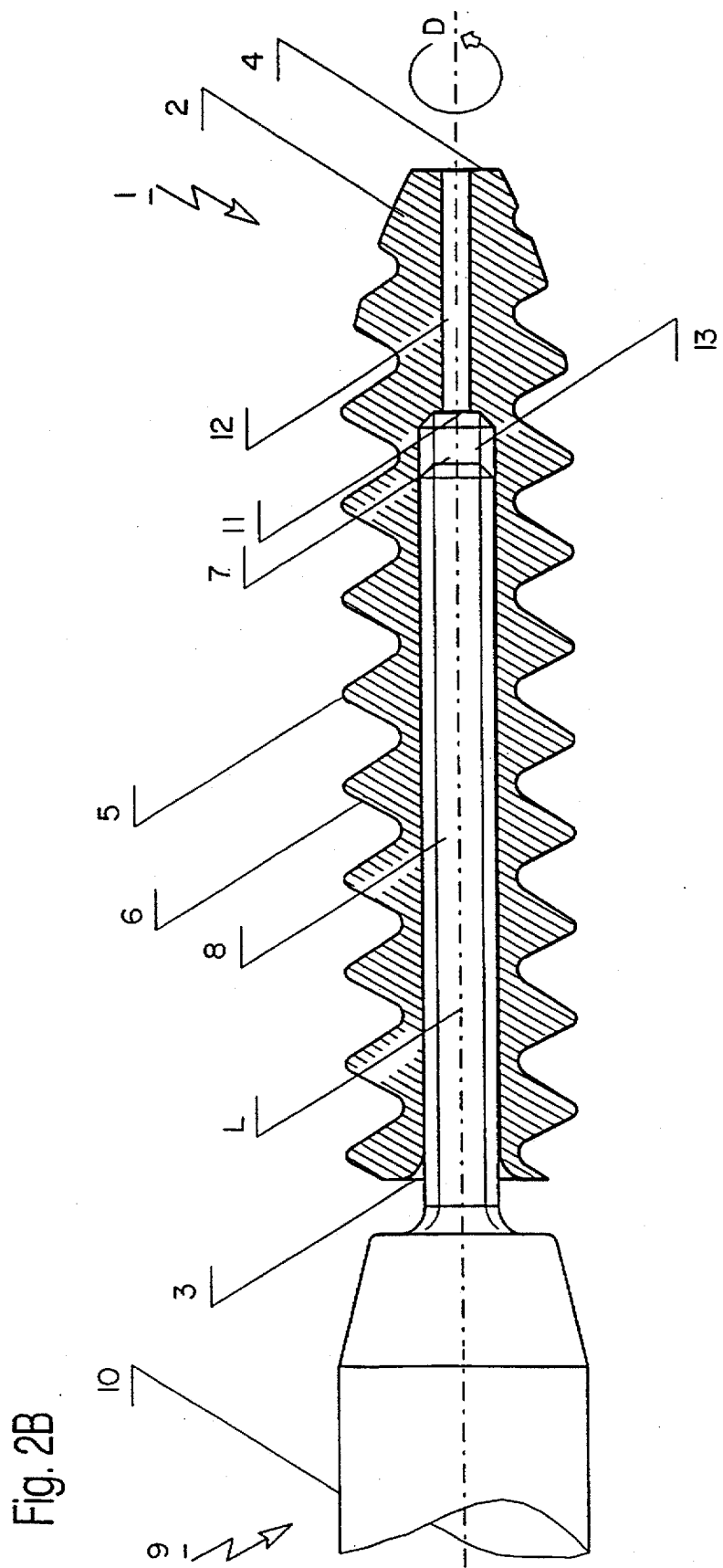
Figure 2C:
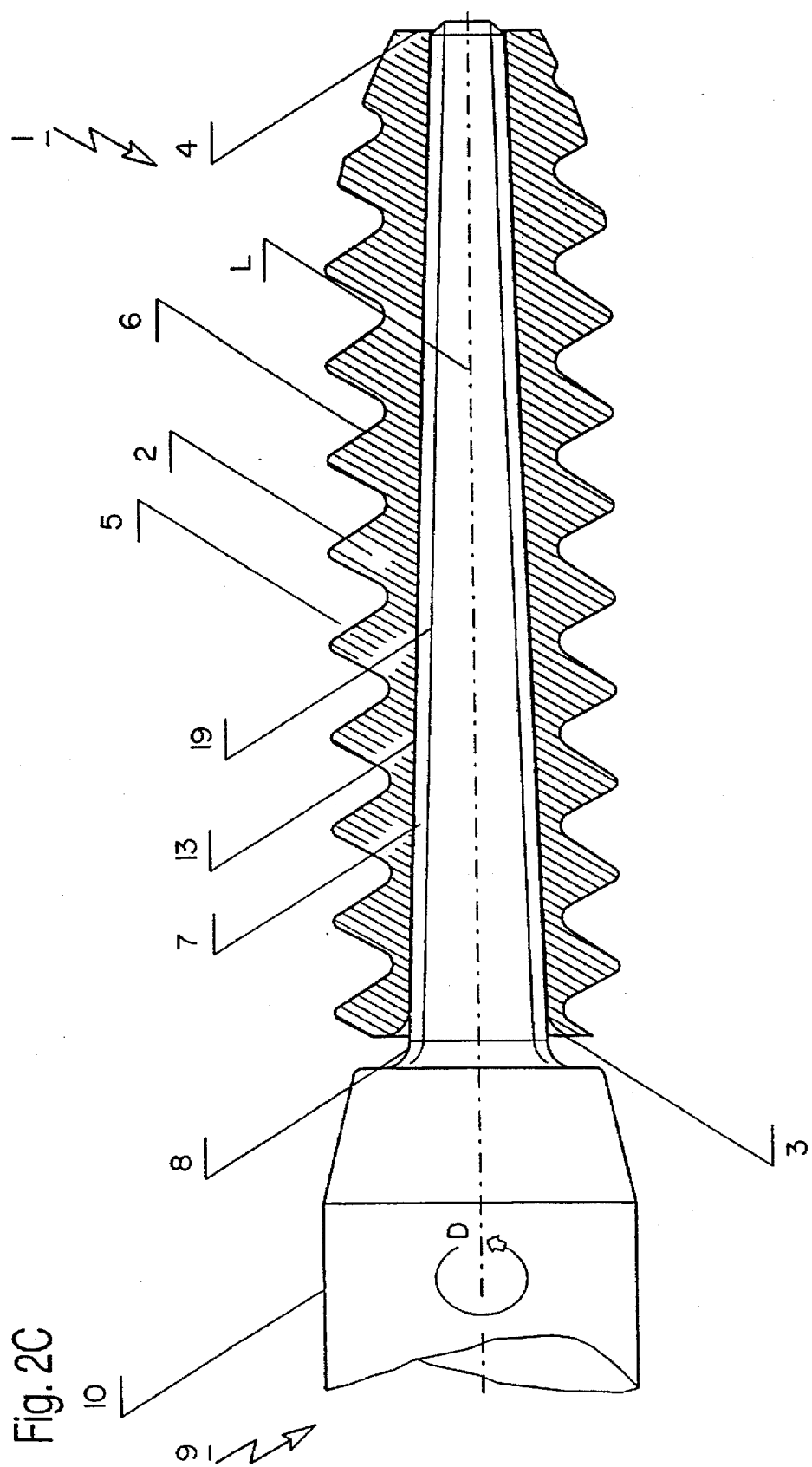

In the embodiments according to FIGS. 1C and 2C and also 1D and 2D, the channel 7 and the shaft 8 have rectilinear generating lines 19 which lie obliquely, i.e. at an angle with respect to the longitudinal axis L, with a semi-aperture angle of 2°. The channel 7 and the shaft 8 can therefore be inscribed in a frustoconical enveloping volume with a semi-aperture angle of 2°.

Figure 1E:
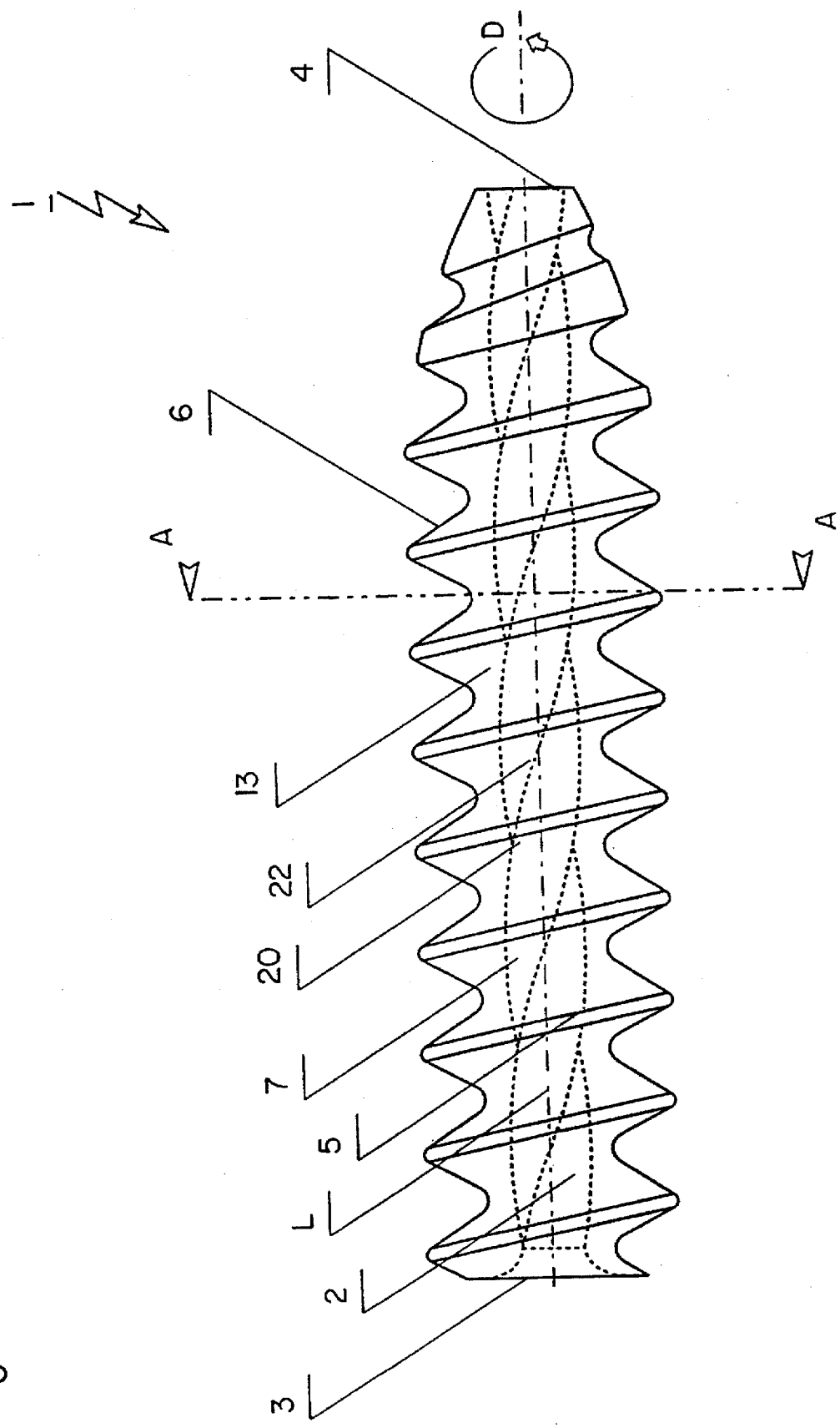
Figure 1F:
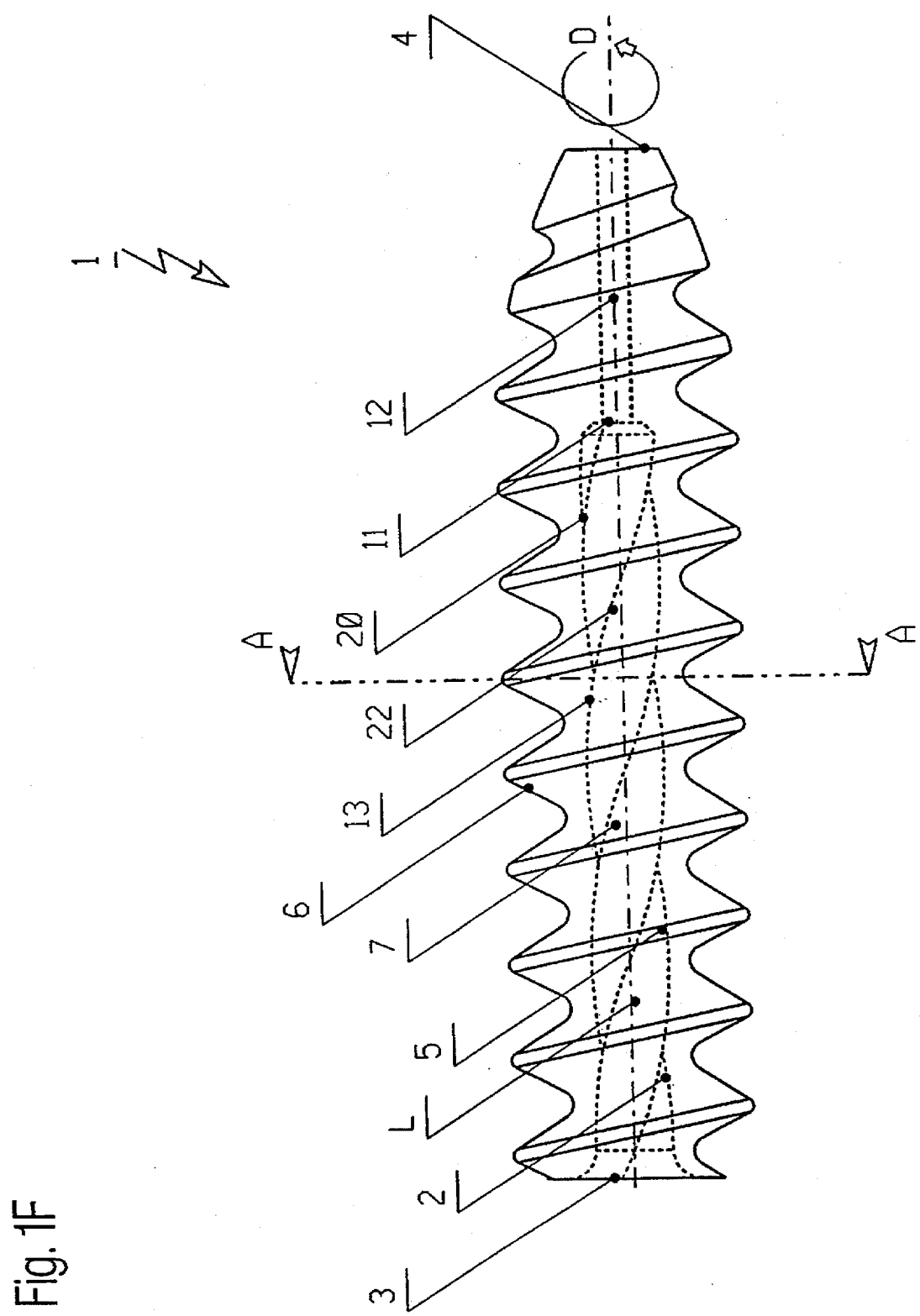
Figure 2E:
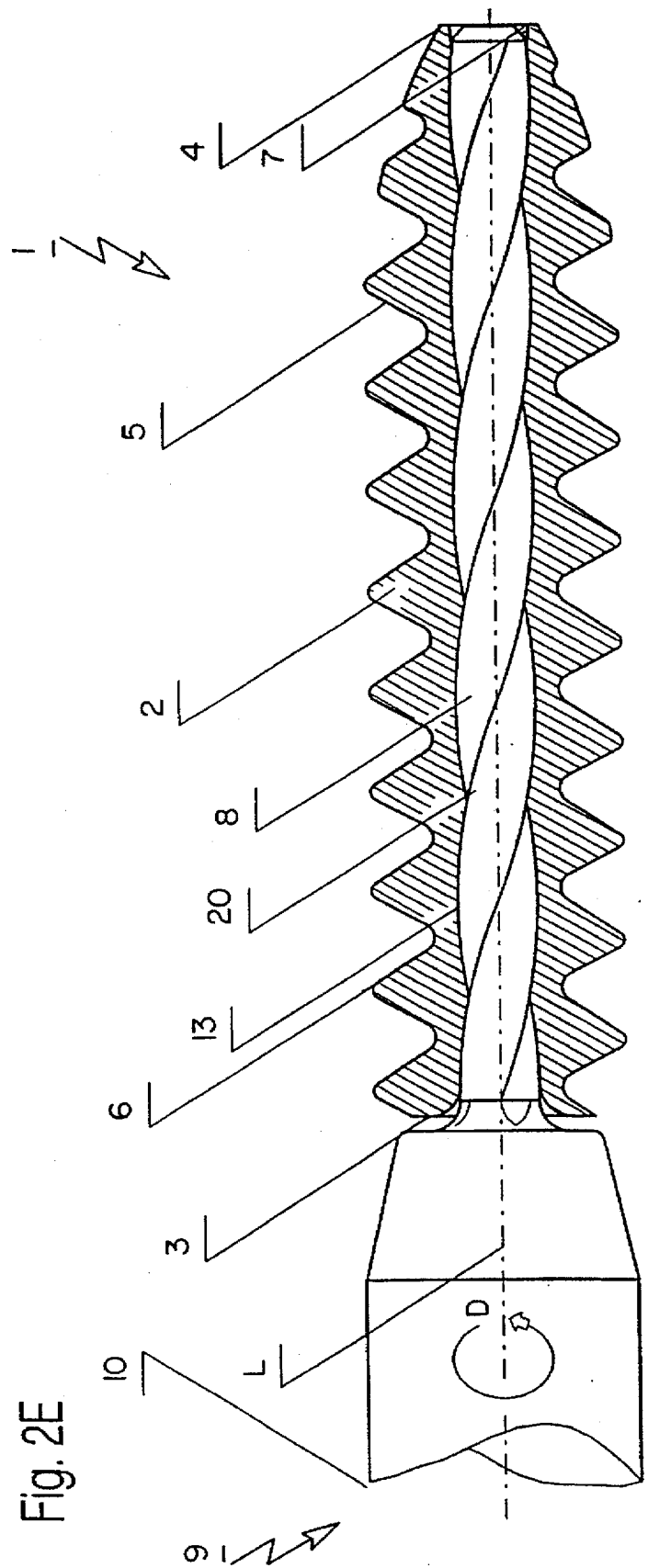
Figure 2F:
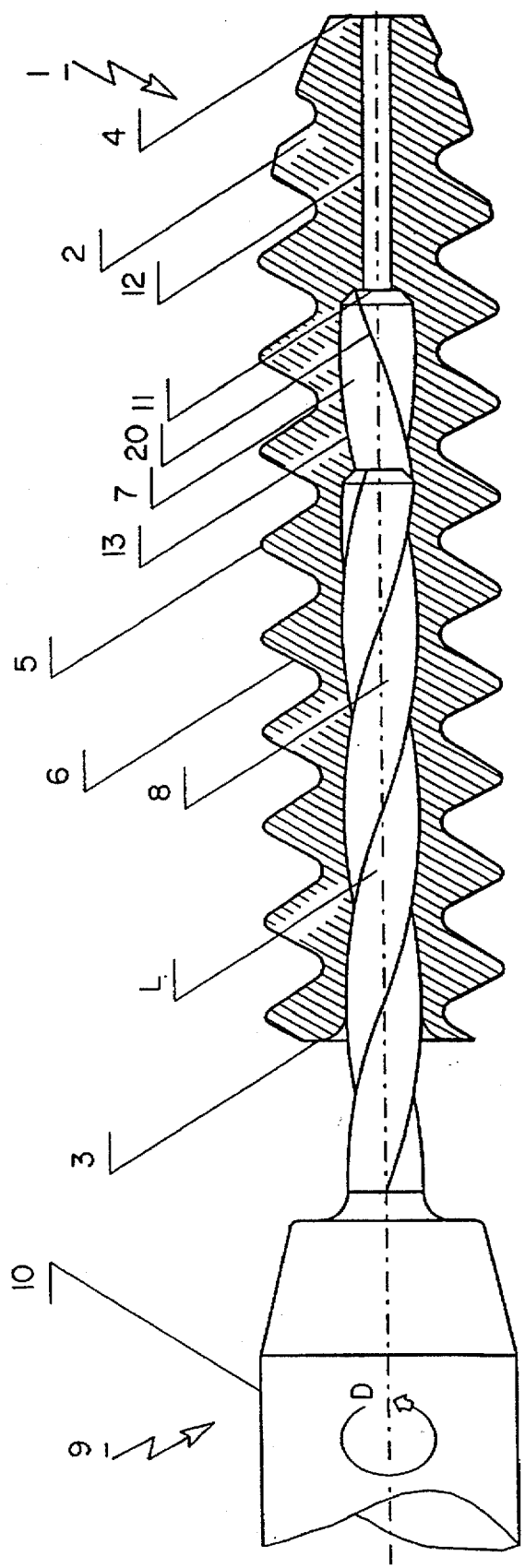

In the embodiments according to FIGS. 1E and 2E and also 1F and 2F, the channel 7 and the shaft 8 have helical generating lines 20 which in each case lie skew with respect to the longitudinal axis L on a cylinder coaxial to the longitudinal axis L. The channel 7 and the shaft 8 can therefore be inscribed in a cylindrical enveloping volume.

Figure 1G:
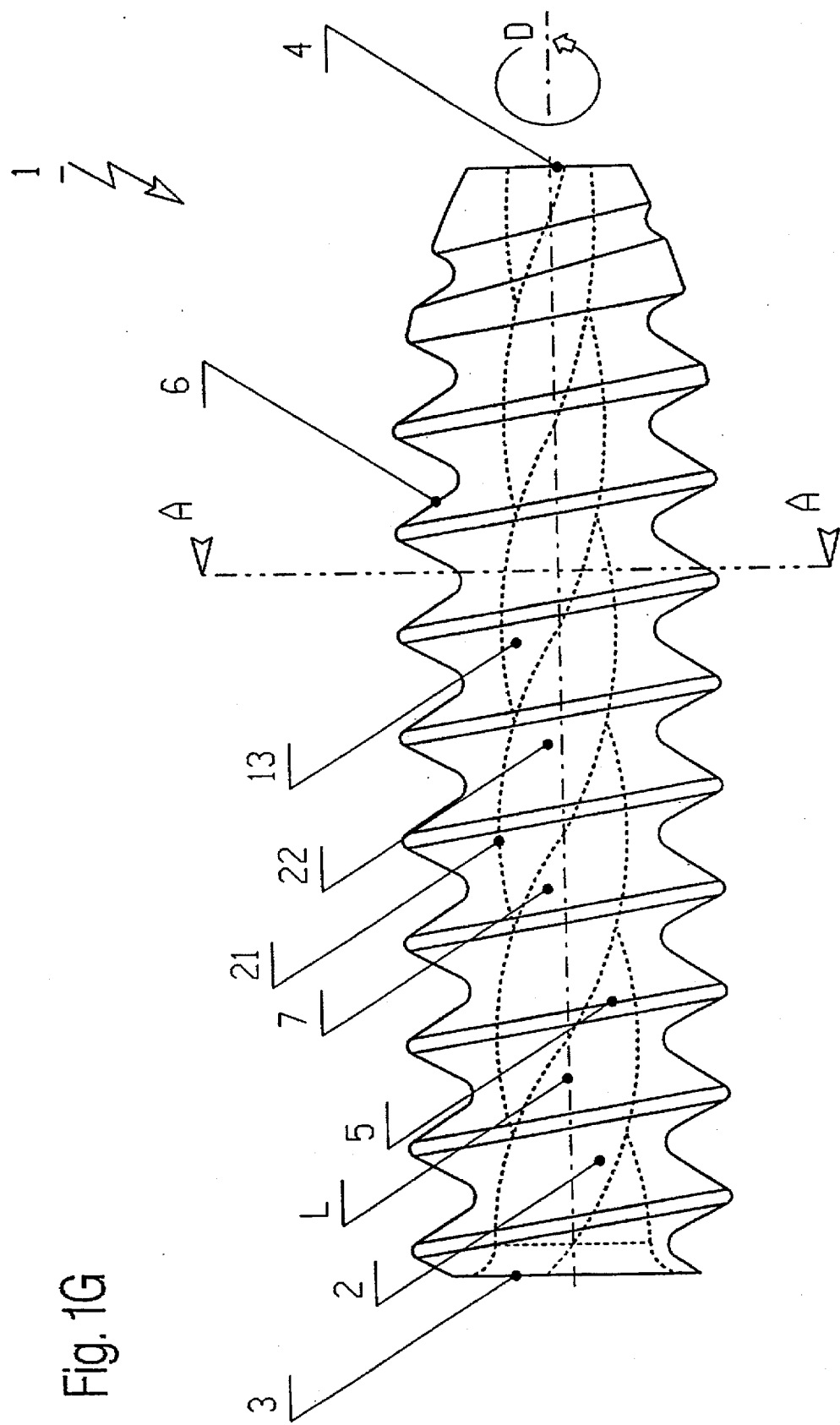
Figure 1H:
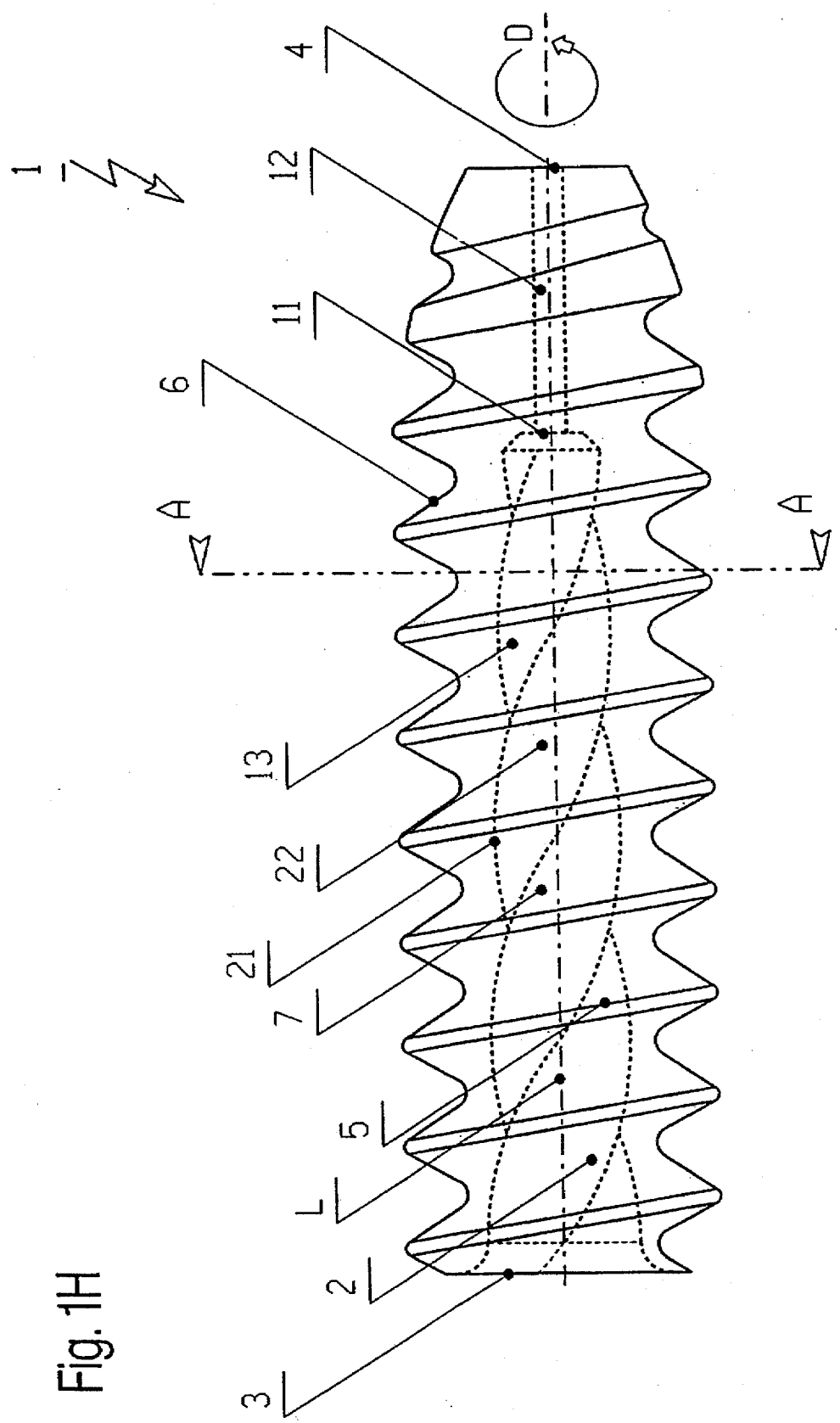
Figure 2G:
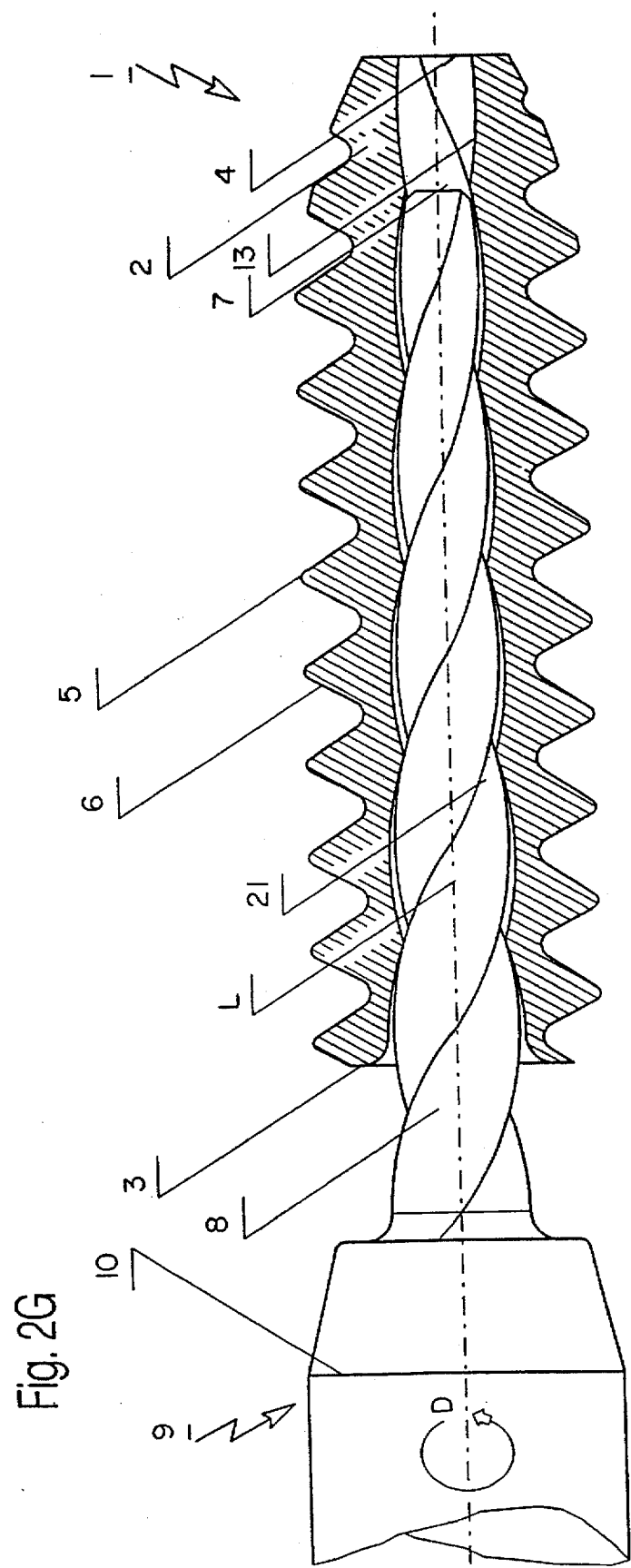
Figure 2H:
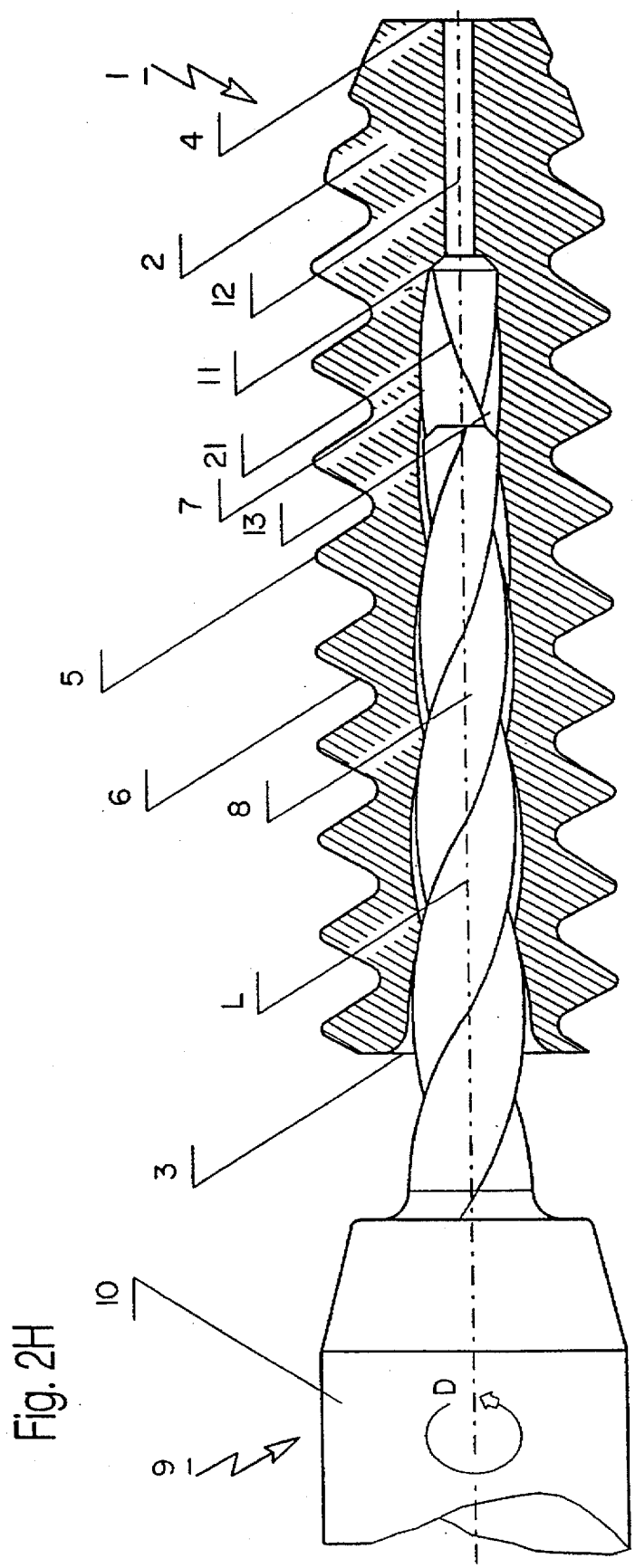

In the embodiments according to FIGS. 1G and 2G and also 1H and 2H, the channel 7 and the shaft 8 have helical generating lines 21 which in each case lie skew with respect to the longitudinal axis L on a truncated cone coaxial to the longitudinal axis L, with a semi-aperture angle of 2°. The channel 7 and the shaft 8 can therefore be inscribed in a frustoconical enveloping volume with a semi-aperture angle of 2°.

FIGS. 3 to 10 show embodiments of the channel wall 13, as trace line thereof, in the plane of a respective cross-section of the screw body 2 at right angles to the longitudinal axis L. In the respective cross-section or in its plane, a trace line 14 corresponds to the longitudinal axis L, a trace line 15 to the outer surface 5 of the screw body 2, a trace line 16 to the external thread 6, and a trace line 17 to the channel wall 13.

Figure 3:
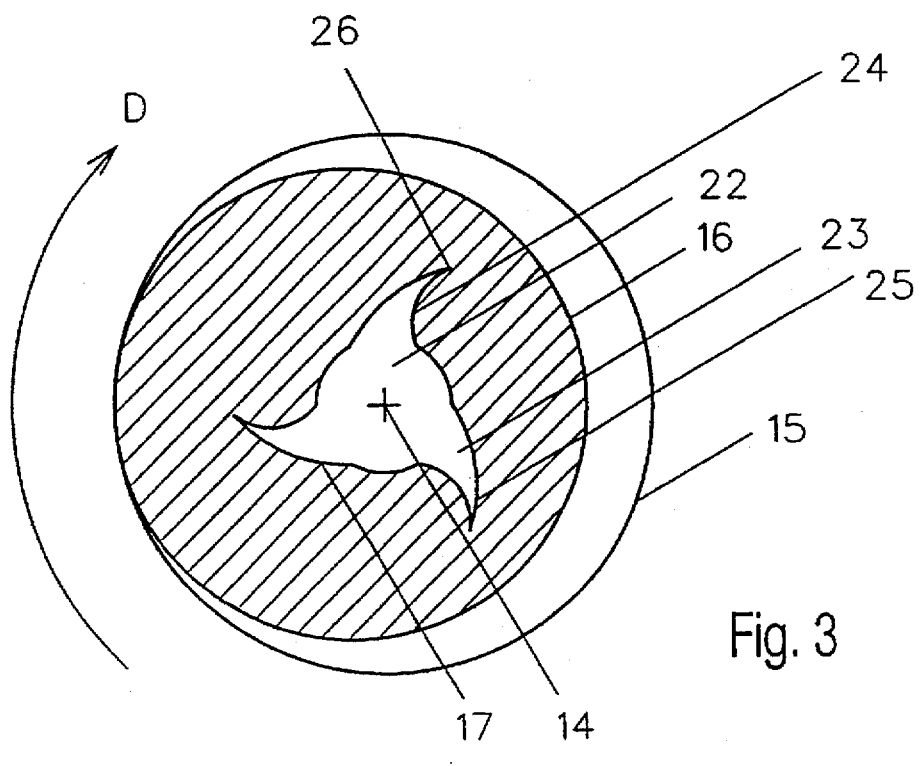
FIGS. 3 to 10 show in each case a cross-section of the screw according to the invention, along the line A—A in FIGS. 1A to 1H, in order to illustrate respective design embodiments of a channel wall of the screw according to the invention.
Figure 4:
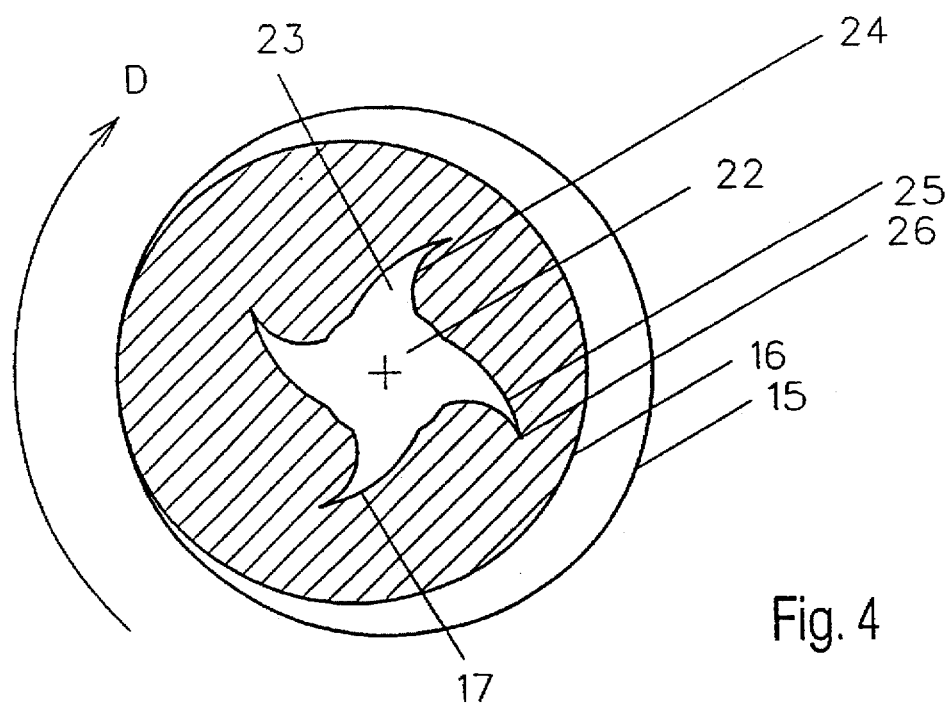
Figure 5:
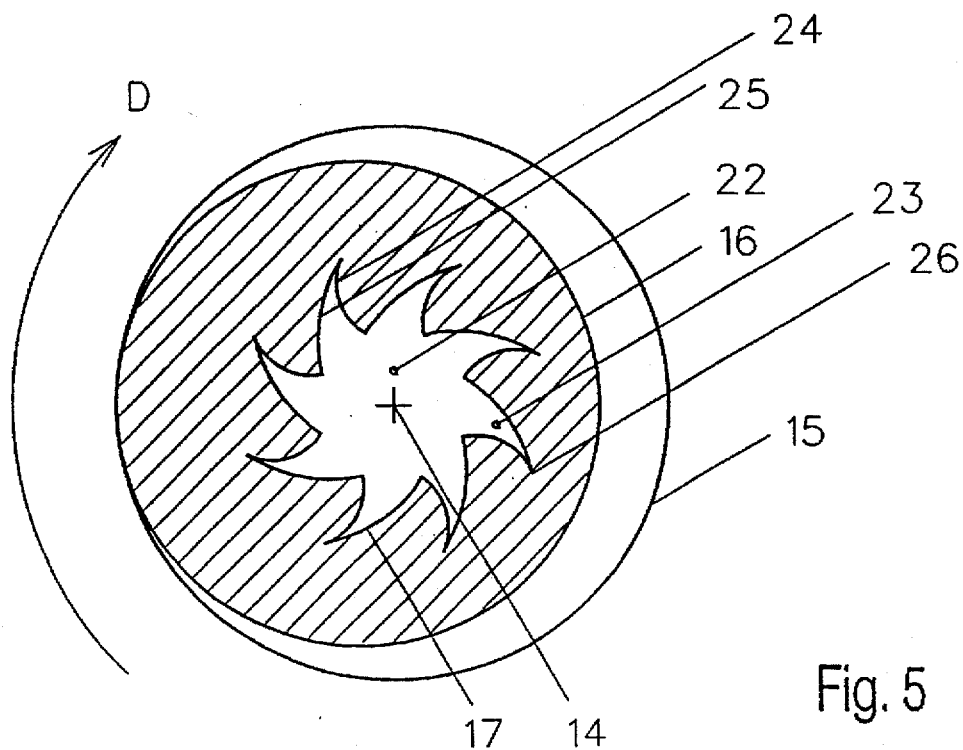
Figure 6:
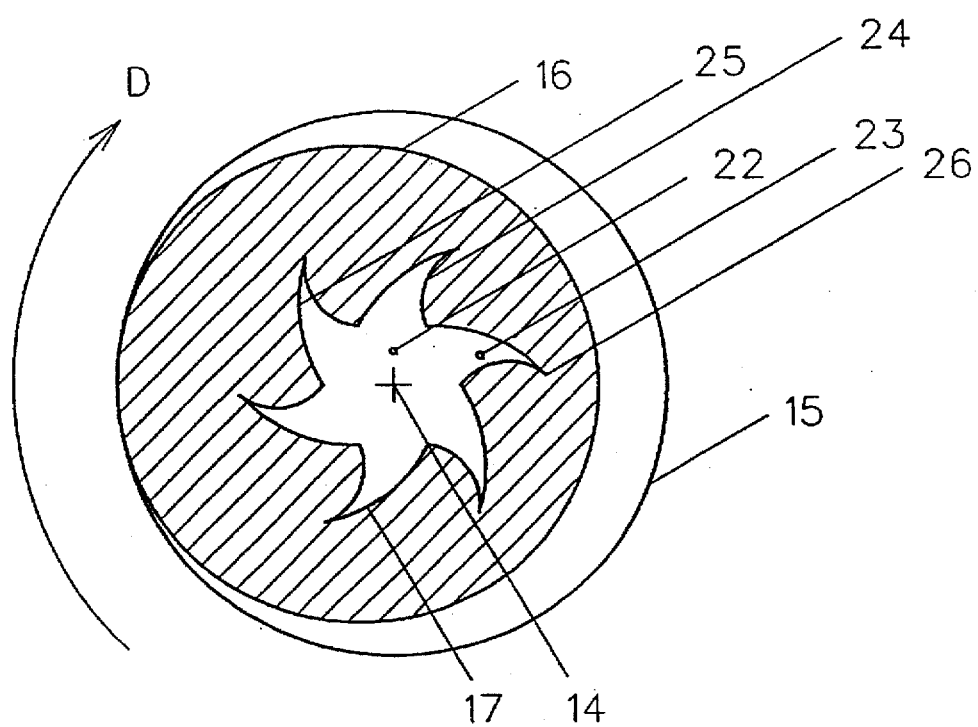
Figure 8:
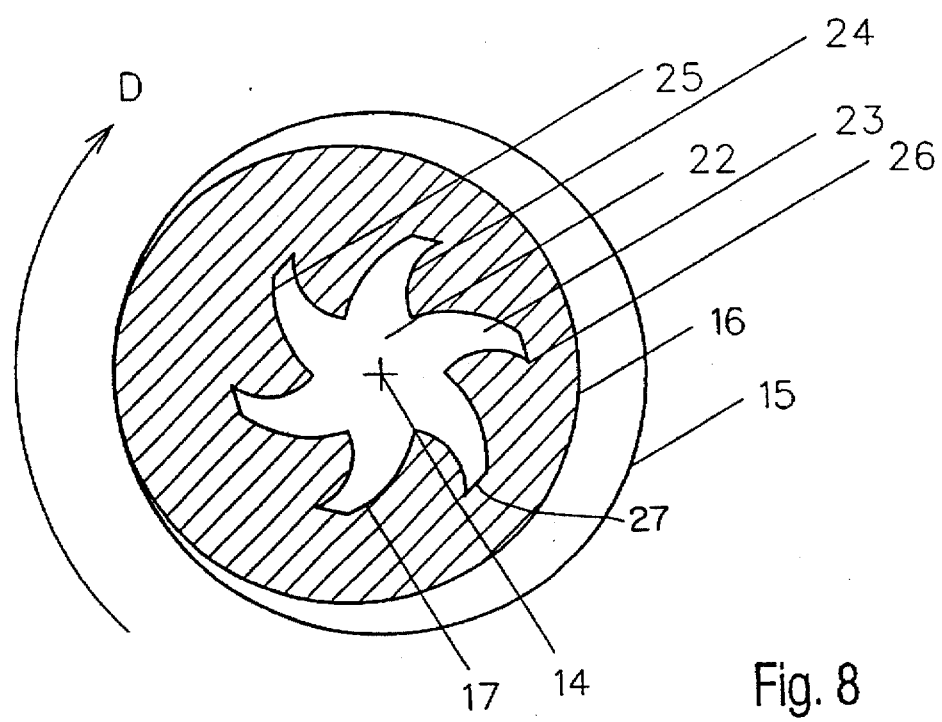
Figure 9:
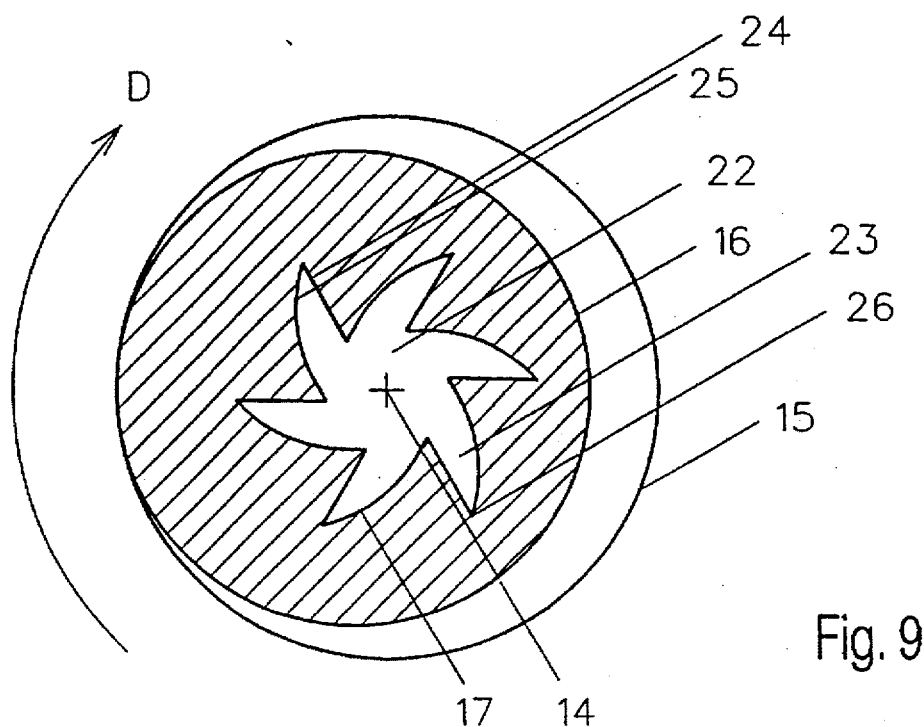
Figure 10:
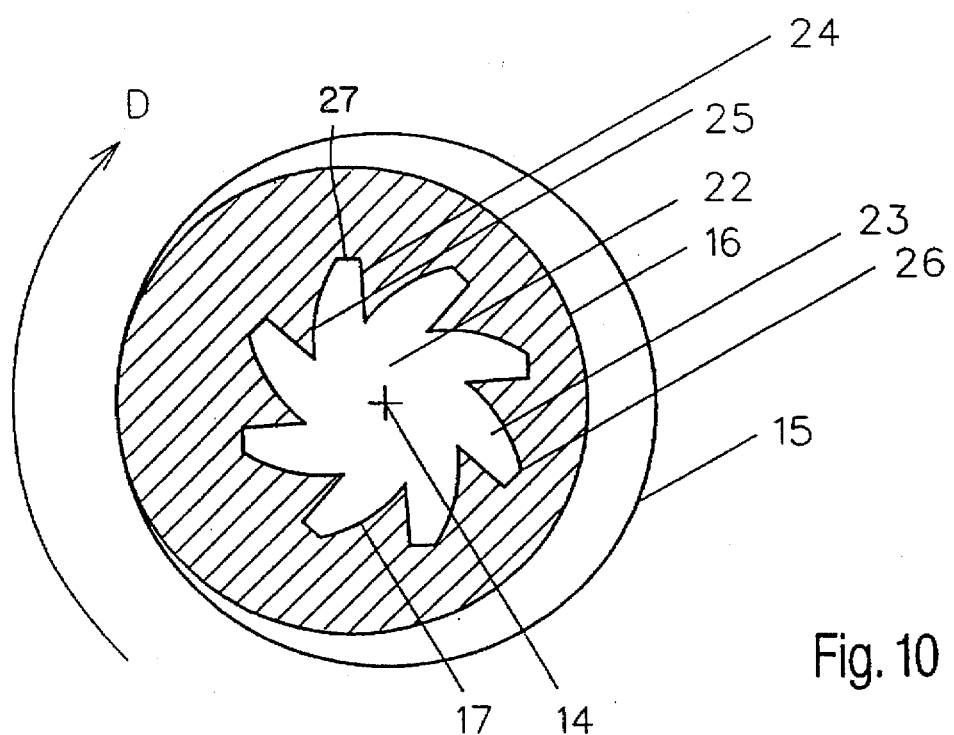
Figure 11:
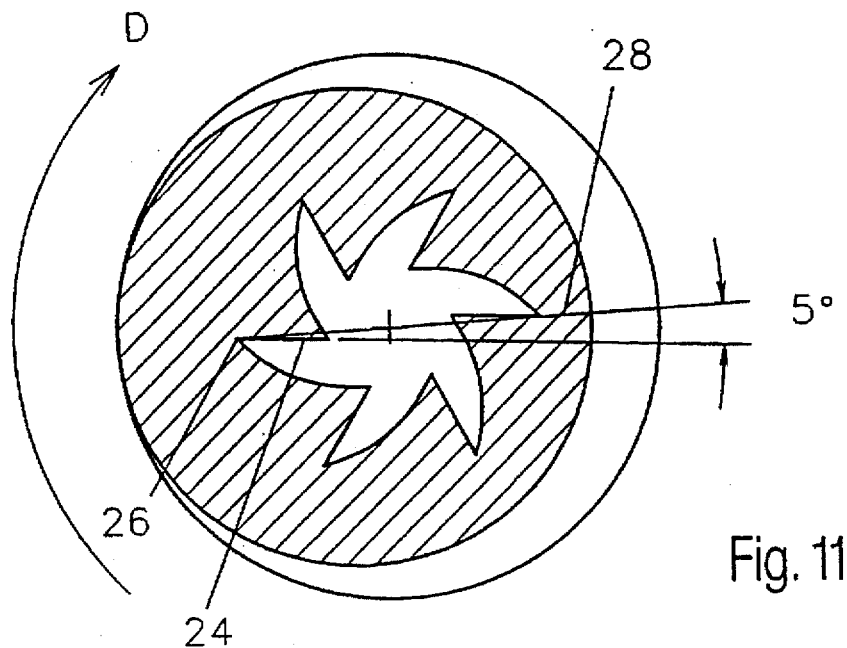
FIGS. 11 and 12 show the same representation as in FIGS. 9 and 10, respectively, with the insertion of only a few reference symbols and the addition of an angle dimension.
Figure 12:
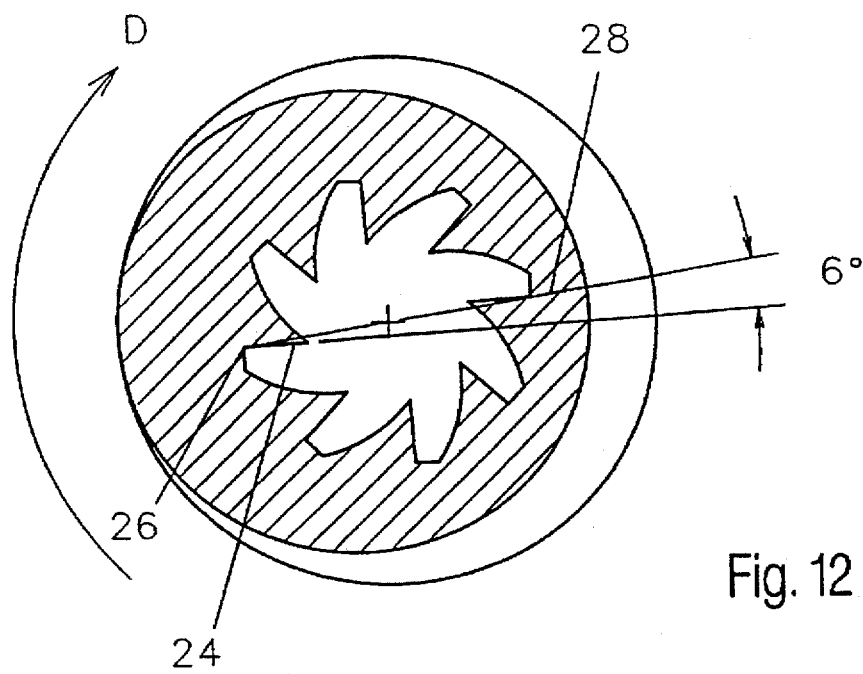

This trace line 17 of the channel wall 13 is a closed contour line which is radially symmetrical, in discrete, regular rotary steps, about a center of symmetry formed by the trace line 14 of the longitudinal axis L, namely, in the embodiment according to FIG. 3, in three rotary steps of 120°, in the embodiment according to FIG. 4 in four rotary steps of 90°, in the embodiments according to FIGS. 5 and 10 in eight rotary steps of 45°, and in the embodiments according to FIGS. 6 to 9 in each case in six rotary steps of 60°. The form of the trace line 17 of the channel wall 13 shows that the channel wall 13 defines, in the channel 7, an axial channel area 22 and a plurality of lobe areas 23 arranged uniformly about the channel area 22, these lobe areas in the embodiment according to FIG. 3 numbering three, in the embodiment according to FIG. 4 numbering four, in the embodiments according to FIGS. 5 and 10 numbering eight, and in the embodiments according to FIGS. 6 to 9 in each case numbering six. Thus, the channel 7 consists essentially of the combination of the axial channel area 22 and the respective lobe areas 23.

In each lobe area 23, the channel wall 13 has a pair of flanks which extend essentially radially outwards starting from the channel area 22. In this pair of flanks, a leading flank and a trailing flank 25 are defined with reference to the direction of rotation D. In the embodiments according to FIGS. 3 to 12, a trace line 24 corresponds to the leading flank and a trace line 25 to the trailing flank.

In the embodiments according to FIGS. 3 to 6, and according to FIG. 9, the trace lines 24 and 25 of the two flanks in each case extend as far as a trace line 26 of an end of the lobe area 23 remote from the channel area 22, so that, viewed spatially, the two flanks run together at the end of the lobe area 23 to form an edge. In the embodiments according to FIGS. 7, 8 and 10, the trace lines 24 and 25 of the two flanks in each case extend into the vicinity of the trace line of that end 26 of the lobe area 23 remote from the channel area 22, but only one of these flanks, namely the leading flank with the trace line 24 in FIGS. 7 and 8, and the trailing flank with the trace line 25 in FIG. 10, extends right up to the trace line 26 of the end of the lobe area 23, so that, viewed spatially, the lobe area 23 ends in a truncated manner and has, in the area of its end, a closure wall with a trace line 27.

An essential feature of the invention in this respect is that in each lobe area 23 at least the leading flank with the trace line 24 exhibits, at least in some areas, a form which leads to an increasing extent in the direction of rotation D as the radial distance from the trace line 14 of the longitudinal axis L increases. In the embodiments according to FIGS. 7, 9 and 10, both flanks with the trace lines 24 and 25 have a form which leads to an increasing extent in the direction of rotation D over the entire radial length thereof as the radial distance increases. In the embodiments according to FIGS. 3 to 6 and according to FIG. 8, the leading flank with the trace line 24 has a form which leads, approximately over a radial outer half of its radial length (in other words in the vicinity of the trace line 26 of the end of the lobe area 23), to an increasing extent in the direction of rotation D as the radial distance increases. In the embodiments according to FIGS. 3 to 10, the trailing flank with the trace line 25 has, at all times, a form which leads to an increasing extent in the direction of rotation D over its entire radial length as the radial distance increases, but the closure wall with the trace line 27 is also to be taken into consideration, which wall, in the stated direction, leads in the embodiment according to FIG. 8 and does not lead in the embodiments according to FIGS. 7 and 10.

It will be made clear here what is meant by "a surface leading in a predetermined direction of rotation with increasing radial distance from an axis". In a cross-section of the surface at right angles to the axis, two points of a trace line of the surface are considered. Starting from the axis, a first radius is directed to the point nearer the axis and a second radius is directed to the point more remote from the axis. In order to make the first radius congruent with the second radius, a turning is required. If this turning is effected in the predetermined direction of rotation, then the trace line or the surface is "leading" in the predetermined direction of rotation, since, in the predetermined direction of rotation, and viewed from the axis, the more remote point lies "ahead" of the nearer point.

In the embodiments according to FIGS. 3 to 6 and according to FIGS. 8 to 10, each lobe area 23 tapers towards its end with the trace line 26. In other words, in these embodiments the two flanks with the trace lines 24 and 25 are at a distance from one another which tapers towards the trace line 26 of the end of the lobe area 23 as the radial distance from the longitudinal axis L increases. This form of the lobe area 23 is obtained by virtue of the fact that, at least in the vicinity of the end of the lobe area 23 with the trace line 26, the leading flank with the trace line 24 is curved concavely with respect to the direction of rotation D, and the trailing flank with the trace line 25 is curved convexly counter to the direction of rotation D. If the two flanks with the trace lines 24 and 25 run together at the end of the lobe area 23 with the trace line 26 to form an edge, this results in a contour line of the trace line 17 of the channel wall 13 having a star-shaped continuous line which is radially symmetrical about the trace line 14 of the longitudinal axis L and has sickle-shaped teeth, of corresponding number, salient with respect to the direction of rotation D. In the opposite case, when the two flanks with the trace lines 24 and 25 do not run together at the end of the lobe area 23 with the trace line 26 to form an edge, this results in a contour line of the trace line 17 of the channel wall 13 having a bucketwheel-shaped continuous line which is radially symmetrical about the trace line 14 of the longitudinal axis L and has approximately sickle-shaped lobes, of corresponding number, salient with respect to the direction of rotation D.

Figure 7:
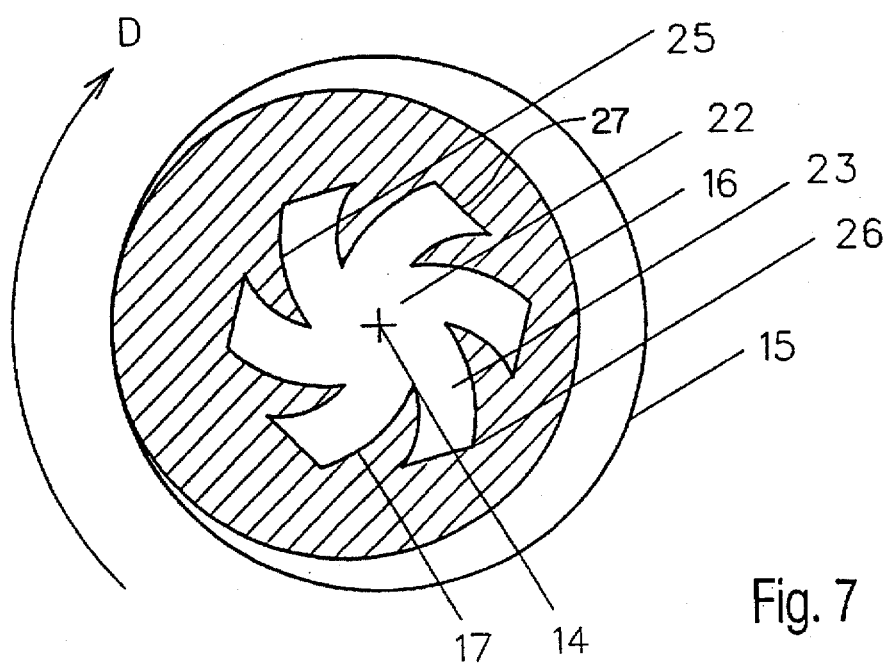

In the embodiment according to FIG. 7, in contrast, each lobe area 23 retains an approximately uniform width since the two flanks with the trace lines 24 and 25 are at an approximately constant distance from one another therein. This results in a contour line of the trace line 17 of the channel wall 13 having a bucketwheel-shaped continuous line which is radially symmetrical about the trace line 14 of the longitudinal axis L and has lobes, of corresponding number, which are salient with respect to the direction of rotation D, have the approximate form of a ring segment and are of approximately constant width.

In the embodiments according to FIGS. 9 and 10, in each lobe area 23 the trace line 24 of the leading flank is inclined essentially in a straight line and with respect to the said direction of rotation. This inclination of the leading flank 24 is up to 10° and is preferably about 5°. The embodiment according to FIG. 9 is represented identically in FIG. 11, and the embodiment according to FIG. 10 is represented identically in FIG. 12, albeit, for reasons of improved clarity, without hatching, and with only a few of the reference symbols, but with an added angle dimension between the trace line 24 of the leading flank and the trace line 28 of a diametral plane passing through the end or through its trace line 26. The value of this angle is, for example in the embodiment according to FIGS. 9 and 11, equal to approximately 5°, and, in the embodiment according to FIGS. 10 and 12, equal to approximately 6°.

FIGS. 13 to 16 show embodiments of the channel wall 13, as trace line thereof, in the plane of a respective cross-section of the screw body 2 at right angles to the longitudinal axis L. In the respective cross-section or in its plane, a trace line 14 corresponds to the longitudinal axis L, a trace line 15 to the outer surface 5 of the screw body 2, a trace line 16 to the external thread 6, and a trace line 17 to the channel wall 13.

This trace line 17 of the channel wall 13 is a closed contour line which is radially symmetrical, in discrete, regular rotary steps, about a center of symmetry formed by the trace line 14 of the longitudinal axis L, namely, in the embodiments shown according to FIGS. 13 to 16 each time in six rotary steps of 60°, which does not exclude other embodiments not shown, for instance in three rotary steps of 120°, in four rotary steps of 90°, in eight rotary steps of 45° etc. The form of the trace line 17 of the channel wall 13 shows that the channel wall 13 defines, in the channel 7, an axial channel area 22 and a plurality of lobe areas 23 arranged uniformly about the channel area 22, these lobe areas in the embodiment according to FIGS. 13 to 16 in each case numbering six, but in other embodiments not shown possibly numbering three, four, eight etc. Thus, the channel 7 consists essentially of the combination of the axial channel area 22 and the respective lobe areas 23.

In each lobe area 23, the channel wall 13 has a pair of flanks which extend essentially radially outwards starting from the channel area 22. In this pair of flanks, a leading flank and a trailing flank 25 are defined with reference to the direction of rotation D. In the embodiments according to FIGS. 13 to 16 a trace line 24 corresponds to the leading flank and a trace line 25 to the trailing flank.

Figure 13:
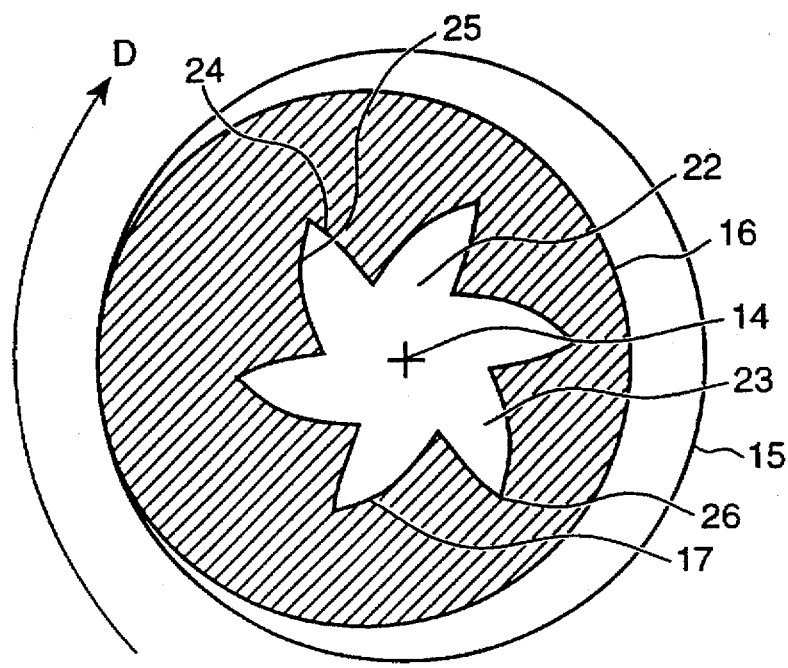
FIGS. 13 to 16 show in each case a cross-section of the screw according to the invention, along the line A—A in FIGS. 1A to 1H, in order to illustrate further respective design embodiments of a channel wall of the screw according to the invention.
Figure 14:
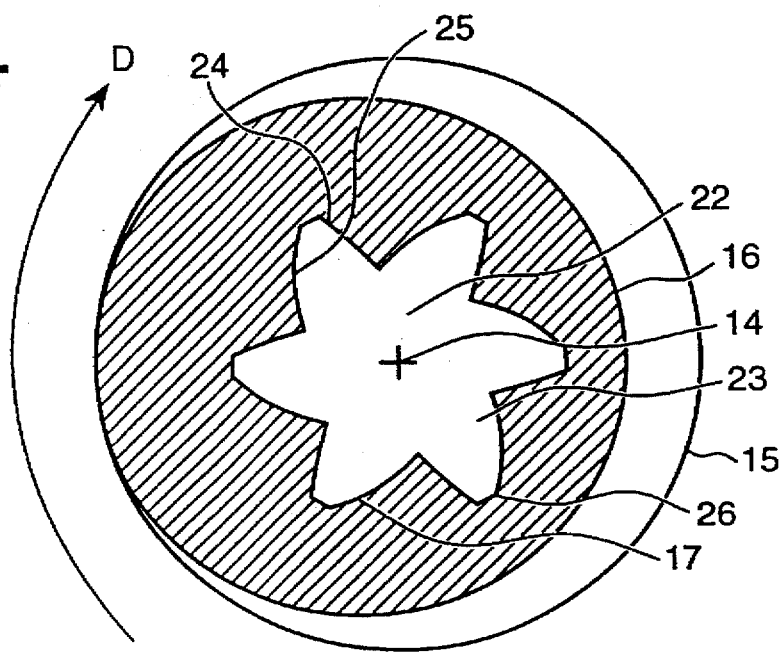
Figure 15:
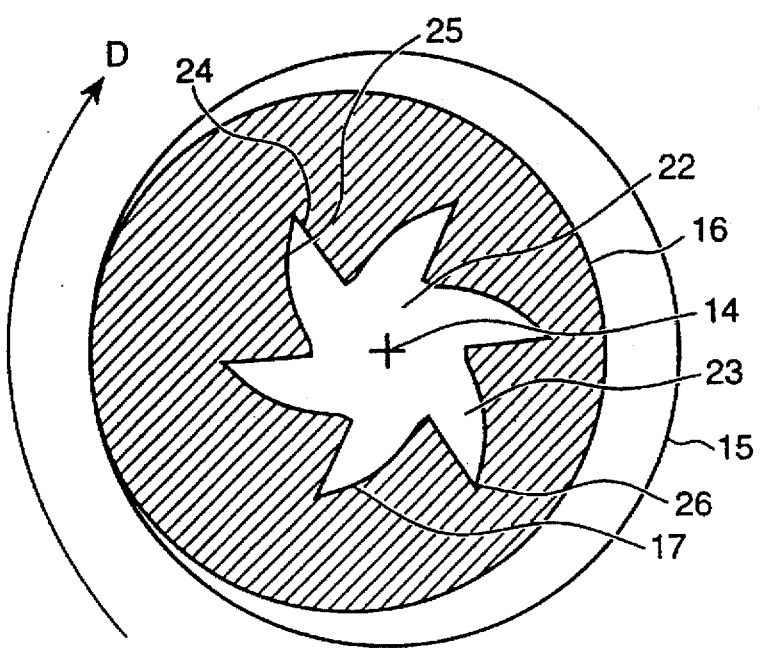
Figure 16:
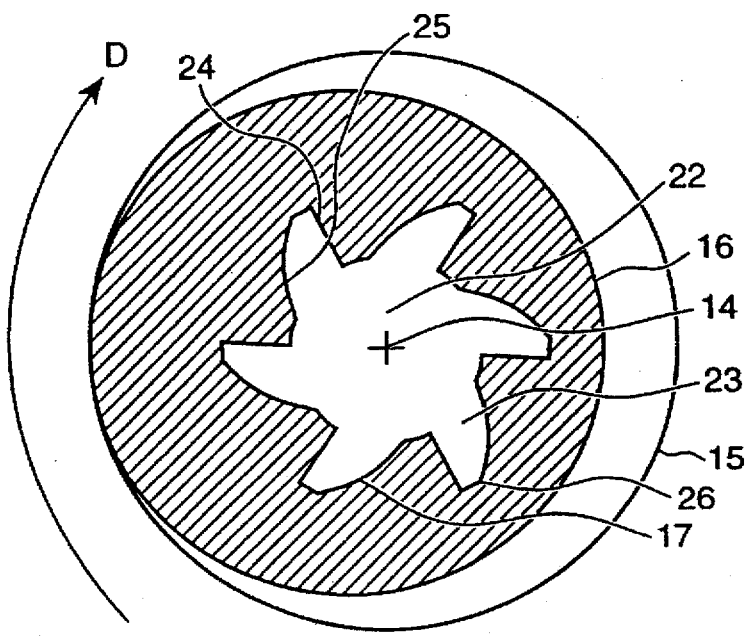

In the embodiments according to FIGS. 13 and 15, the trace lines 24 and 25 of the two flanks in each case extend as far as a trace line 26 of an end of the lobe area 23 remote from the channel area 22, so that, viewed spatially, the two flanks run together at the end of the lobe area 23 to form an edge. In the embodiments according to FIGS. 14 and 16, the trace lines 24 and 25 of the two flanks in each case extend into the vicinity of the trace line of that end 26 of the lobe area 23 remote from the channel area 22, but only one of these flanks, namely the trailing flank with the trace line 25, extends right up to the trace line 26 of the end of the lobe area 23, so that, viewed spatially, the lobe area 23 ends in a truncated manner and has, in the area of its end, a closure wall with a trace line 27.

An essential feature of the invention in this respect is that in the shown cross-section of the screw body 2 at right angles to the longitudinal axis L, each lobe area 23 is formed asymmetrical in respect of a diametrical plane passing through the longitudinal axis L. To give each lobe area 23 a sawtooth-like profile (of a radial distance of the contour line 17 from the longitudinal axis L when considered along the contour line 17) with, on the average, a steeper raise of the leading flank 24 and a flatter fall of the trailing flank 25, as shown a section of the contour line 17 which corresponds to the leading flank 24 is formed shorter than a section of the contour line 17 which corresponds to the trailing flank 25.

In the embodiments according to FIGS. 13 to 16, each lobe area 23 tapers towards its end with the trace line 26. In other words, in these embodiments the two flanks with the trace lines 24 and 25 are at a distance from one another which tapers towards the trace line 26 of the end of the lobe area 23 as the radial distance from the longitudinal axis L increases. This form of the lobe area 23 is obtained by virtue of the fact that, at least in the vicinity of the end of the lobe area 23 with the trace line 26, the leading flank with the trace line 24 is curved with respect to the direction of rotation D less convexly i.e. on the average with a larger radius of curvature than the trailing flank with the trace line 25 is curved convexly counter to the direction of rotation D. In this connection, a planar embodiment of the leading flank with the trace line 24 has to be understood as a limiting case in which the convex trace line has an infinitely large radius of curvature. If the two flanks with the trace lines 24 and 25 run together at the end of the lobe area 23 with the trace line 26 to form an edge, this results in a contour line of the trace line 17 of the channel wall 13 having a pointed star-shaped continuous line which is radially symmetrical about the trace line 14 of the longitudinal axis L and has teeth of corresponding number, salient with respect to the direction of rotation D. In the opposite case, when the two flanks with the trace lines 24 and 25 do not run together at the end of the lobe area 23 with the trace line 26 to form an edge, this results in a contour line of the trace line 17 of the channel wall 13 having a blunt continuous line which is radially symmetrical about the trace line 14 of the longitudinal axis L and has lobes of corresponding number, salient with respect to the direction of rotation D.

If the channel 7 has, as in the embodiments according to FIGS. 1A and 2A and also 1B and 2B, generating lines 18 which are rectilinear and parallel with respect to the longitudinal axis L, then the leading flank lies essentially in one plane, and the contour lines or trace lines 17 of the channel wall 13, in two cross-sections of the screw body 2 which are different from one another and at right angles to the longitudinal axis L, are congruent with one another.

If the channel 7 has, as in the embodiments according to FIGS. 1C and 2C and also 1D and 2D, generating lines 19 which are rectilinear and lie obliquely with respect to the longitudinal axis L, then the leading flank is tapered in the direction from the proximal end 3 to the distal end 4, and the contour lines or trace lines 17 of the channel wall 13, in two cross-sections of the screw body 2 which are different from one another and at right angles to the longitudinal axis L, are images of one another which can be made congruent by homothetic transformation about the trace line 14 of the longitudinal axis L.

If the channel 7 has, as in the embodiments according to FIGS. 1E and 2E and also 1F and 2F, generating lines 20 which are twisted helically about the longitudinal axis L with respect to the direction of rotation D, then the leading flank is also twisted helically about the longitudinal axis L with respect to the direction of rotation D, and the contour lines or trace lines 17 of the channel wall 13, in two cross-sections of the screw body 2 which are different from one another and at right angles to the longitudinal axis L, are congruence images of one another which can be made congruent by simple turning about the trace line 14 of the longitudinal axis L.

Finally, if the channel 7 has, as in the embodiments according to FIGS. 1G and 2G and also 1H and 2H, generating lines 21 which are twisted helically about the longitudinal axis L with respect to the direction of rotation D and at the same time lie skew with respect to the longitudinal axis L, then the leading flank is also both helically twisted about the longitudinal axis L with respect to the direction of rotation D and tapered in the direction from the proximal end 3 to the distal end 4, and the contour lines or trace lines 17 of the channel wall 13, in two cross-sections of the screw body 2 which are different from one another and at right angles to the longitudinal axis L, are images of one another which can be made congruent by a combination of simple turning and homothetic transformation about the trace line 14 of the longitudinal axis L.

In the case of the twisting, the pitch is, for example, one turn in 10 cm. In the case of the tapering, the semi-aperture angle is up to 10° and preferably about 2°.

Since the shaft 8 of the screwdriver 9 for driving a screw 1 into bone material of a patient during bone surgery must be capable of being introduced into the channel 7 and removed therefrom, the shaft 8 has a form which matches the channel 7 in a complementary manner and which corresponds to the embodiments of the screw described above and, having a contour of corresponding cross-section, can be cylindrical or frustoconical and rectilinear or twisted.

The described embodiments of the screw and of the corresponding shaft of the screwdriver with in each case 3 to 8 teeth or lobes are in fact preferred, and embodiments with 6 teeth or lobes are particularly preferred. However, it should be understood that the invention also covers embodiments of the screw and of the corresponding shaft of the screwdriver with only 2 or with more than 8 teeth or lobes, for example with 9, 10 or more teeth or lobes.

What is claimed is:

1. A screw made of biodegradable material for bone surgery purposes, comprising:

an elongate screw body which extends, in the direction of a longitudinal axis thereof, between a proximal and a distal end thereof;

an outer surface of the screw body being provided with an external thread coaxial with respect to the longitudinal axis, which external thread is configured for guiding and holding the screw on bone material of a patient and defines a direction of rotation about the longitudinal axis for the screwing-in of the screw body and the advancing of the distal end into the bone material;

an elongate channel coaxial with respect to the longitudinal axis and provided in the screw body, which channel is open at the proximal end for receiving a shaft of a screwdriver for turning the screw;

the channel having a channel wall, the shape of which is radially symmetrical about the longitudinal axis in discrete, regular rotary steps and provides, in a cross-section of the screw body at right angles to the longitudinal axis, a trace line which is a closed contour line radially symmetrical about a trace line of the longitudinal axis in discrete, regular rotary steps;

the channel wall defining an axial channel area and a plurality of lobe areas arranged uniformly about the channel area, so that the channel consists essentially of the combination of the axial channel area and the lobe areas;

in each lobe area, the channel wall having a pair of flanks which extend essentially from the channel area to the vicinity of an end of the lobe area remote from the channel area, and which, with reference to the said direction of rotation, define in each case a leading flank and a trailing flank;

the channel extending into the area of the distal end of the screw, and in a cross-section of the screw body at right angles to the longitudinal axis, each lobe area being formed asymmetrically in the respect of a diametrical plane passing through the longitudinal axis, a section of the contour line which corresponds to the leading flank being shorter than a section of the contour line which corresponds to the trailing flank, so that the lobe area has a sawtooth-like profile of a radial distance of the contour line from the longitudinal axis, when considered along the contour line with, on the average, a steeper raise of the leading flank and a flatter fall of the trailing flank.

2. The screw according to claim 1, wherein:

in each lobe area, at least one of the said flanks has, at least in the vicinity of the said remote end of the lobe area, a form which leads to an increasing extent in the said direction of rotation as the radial distance from the longitudinal axis increases.

3. The screw according to claim 1, wherein:

the flanks are twisted helically about the longitudinal axis with respect to said direction of rotation, in such a way that, in two cross-sections of the screw body which are different from one another and at right angles to the longitudinal axis, the contour lines represent congruent images of one another which can be made congruent by simple turning about the trace line of the longitudinal axis.

4. The screw according to claim 1, wherein:

the flanks are tapered in the direction from the proximal end to the distal end in such a way that, in two cross-sections of the screw body which are different from one another and at right angles to the longitudinal axis, the contour lines represent images of one another which can be made congruent by homothetic transformation about the trace line of the longitudinal axis.

5. The screw according to claim 4, wherein:

the flanks are both twisted and tapered in such a way that, in two cross-sections of the screw body which are different from one another and at right angles to the longitudinal axis, the contour lines represent images of one another which can be made congruent by a combination of simple turning and homothetic transformation about the trace line of the longitudinal axis.

6. The screw according to claim 4, wherein:

the tapering of the flanks in the direction from the proximal end to the distal end corresponds to a semi-aperture angle of up to 10°.

7. The screw according to claim 2, wherein:

in each lobe area, the two flanks extend at a distance from one another which tapers towards the remote end of the lobe area as the radial distance from the longitudinal axis increases.

8. The screw according to claim 7, wherein:

the two flanks run together at the remote end of the lobe area to form an edge.

9. The screw according to claim 2, wherein:

in each lobe area, the trailing flank is curved convexly counter to the said direction of rotation, at least in the vicinity of said remote end of the lobe area.

10. The screw according to claim 1, wherein:

in each lobe area, the leading flank is curved convexly with respect to the said direction of rotation, or the leading flank is essentially located in a plane passing through the longitudinal axis.

11. The screw according to claim 2, wherein:

in each lobe area, the leading flank is curved concavely with respect to the said direction of rotation, at least in the vicinity of said remote end of the lobe area.

12. The screw according to claim 2, wherein:

in a cross-section of the screw body at right angles to the longitudinal axis, the contour line corresponds essentially to a star-shaped continuous line which is radially symmetrical about the trace line of the longitudinal axis, with 3 to 8 lobes salient with respect to said direction of rotation.

13. The screw according to claim 12, wherein:

the lobes are approximately sickle-shaped.

14. The screw according to claim 2, wherein:

in each lobe area, the two flanks extend at an approximately constant distance from one another.

15. The screw according to claim 14, wherein:

in a cross-section of the screw body at right angles to the longitudinal axis, the contour line corresponds essentially to a bucketwheel-shaped continuous line which is radially symmetrical about the trace line of the longitudinal axis, with 3 to 8 lobes, which are salient with respect to the said direction of rotation, are approximately in the form of a ring segment, and are of approximately constant width.

16. The screw according to claim 2, wherein:

a trace line of the leading flank is inclined essentially in a straight line and with respect to the said direction of rotation in each lobe area, in a cross-section of the screw body at right angles to the longitudinal axis.

17. The screw according to claim 16, wherein:

the inclination of the leading flank is up to 10° from a diametric line across the cross-section of the screw body.

18. The screw according to claim 6, wherein:

said semi-aperture angle is approximately 2°.

19. The screw according to claim 17, wherein:

the inclination of said leading flank is about 5°.

20. A screwdriver for driving a screw that is made of biodegradable material, for bone surgery purposes, the screw having:

an elongate screw body which extends, in the direction of a longitudinal axis thereof, between a proximal and a distal end thereof;

an outer surface of the screw body being provided with an external thread coaxial with respect to the longitudinal axis, which external thread is for guiding and holding the screw on bone material of a patient and defines a direction of rotation about the longitudinal axis for the screwing-in of the screw body and the advancing of the distal end into the bone material;

an elongate channel coaxial with respect to the longitudinal axis and provided in the screw body, which channel is open at the proximal end for receiving a shaft of a screwdriver for turning the screw;

the channel having a channel wall, the shape of which is radially symmetrical about the longitudinal axis in discrete, regular rotary steps and provides, in a cross-section of the screw body at right angles to the longitudinal axis, a trace line which is a closed contour line radially symmetrical about a trace line of the longitudinal axis in discrete, regular rotary steps;

the channel wall defining an axial channel area and a plurality of lobe areas arranged uniformly about the channel area, so that the channel consists essentially of the combination of the axial channel area and the lobe areas;

in each lobe area, the channel wall having a pair of flanks which extend essentially from the channel area to the vicinity of an end of the lobe area remote from the channel area, and which, with reference to the said direction of rotation, define in each case a leading flank and a trailing flank;

the channel extending into the area of the distal end of the screw, and in a cross-section of the screw body at right angles to the longitudinal axis, each lobe area being formed in the respect of a diametrical plane passing through the longitudinal axis, a section of the contour line which corresponds to the leading flank being shorter than a section of the contour line which corresponds to the trailing flank, so that the lobe area has a sawtooth-like profile of a radial distance of the contour line from the longitudinal axis, when considered along the contour line with, on the average, a steeper raise of the leading flank and a flatter fall of the trailing flank, for driving the screw into bone material of a patient during bone surgery, said screwdriver comprising:

a grip and an elongate shaft secured to said shaft;

said shaft being configured to be introduced into the channel of the screw and removed therefrom;

said shaft having a form matching the channel of the screw in a complementary manner.

* * * * *